(12) United States Patent
Reisfeld

(10) Patent No.: US 6,226,542 B1
(45) Date of Patent: May 1, 2001

(54) THREE-DIMENSIONAL RECONSTRUCTION OF INTRABODY ORGANS

(75) Inventor: Daniel Reisfeld, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 0 days.

(21) Appl. No.: 09/122,137

(22) Filed: Jul. 24, 1998

(51) Int. Cl.$^7$ ........................................................ A61B 5/05

(52) U.S. Cl. .......................... 600/407; 600/417; 600/420; 600/481; 600/513; 606/130; 364/413.06; 364/468.25

(58) Field of Search .................... 364/413.06, 468.25; 600/371, 372, 373, 374, 377, 380, 381, 382, 383, 384, 407, 417, 420, 481, 508–526; 606/130

(56) References Cited

U.S. PATENT DOCUMENTS

| | | | |
|---|---|---|---|
| 3,316,896 | 5/1967 | Thomasset | 128/2.1 |
| 4,522,212 | 6/1985 | Gelinas et al. | 128/642 |
| 4,628,937 | 12/1986 | Hess et al. | 128/642 |
| 4,660,571 | 4/1987 | Hess et al. | 128/784 |
| 4,682,603 | 7/1987 | Franz | 128/642 |
| 4,699,147 | 10/1987 | Chilson et al. | 128/642 |
| 4,762,124 | 8/1988 | Kerch et al. | 128/156 |
| 4,892,104 | 1/1990 | Ito et al. | 128/697 |
| 4,898,181 | 2/1990 | Kessler | 128/699 |
| 4,905,705 | 3/1990 | Kizakevich et al. | 128/696 |
| 4,911,174 | 3/1990 | Pederson et al. | 128/695 |
| 4,922,912 | 5/1990 | Watanabe | 128/642 |
| 4,940,064 | 7/1990 | Desai | 128/784 |
| 4,955,382 | 9/1990 | Franz et al. | 128/642 |
| 4,962,767 | 10/1990 | Brownlee | 128/786 |
| 4,979,510 | 12/1990 | Franz et al. | 128/642 |
| 5,022,396 | 6/1991 | Watanabe | 128/642 |
| 5,038,791 | 8/1991 | Collins et al. | 128/696 |
| 5,127,403 | 7/1992 | Brownlee | 128/419 P |
| 5,146,926 | 9/1992 | Cohen | 128/710 |
| 5,156,151 | 10/1992 | Imran | 128/642 |
| 5,215,103 | 6/1993 | Desai | 128/784 |
| 5,228,442 | 7/1993 | Imran | 128/642 |
| 5,231,995 | 8/1993 | Desai | 128/784 |
| 5,239,999 | 8/1993 | Imran | 128/642 |
| 5,243,981 | 9/1993 | Hudrlik | 607/11 |
| 5,255,678 | 10/1993 | Deslauriers et al. | 128/642 |
| 5,255,679 | 10/1993 | Imran | 128/642 |
| 5,279,299 | 1/1994 | Imran | 128/642 |

(List continued on next page.)

OTHER PUBLICATIONS

Gerstenfeld E., Sahakian A., Baerman J., Ropella K., Swiryn S. (1991) "Detection of Changes in Atrial Endocardial Activation With Use of an Orthogonal Catheter", JACC. vol. 18, No. 4: 1034–42.

Gerstenfeld E., Sahakian A., Swiryn S. (1992) "Evidence for Transient Linking of Atrial Excitation During Atrial Fibrillation in Humans", Circulation. vol. 86, No. 2: 375–382.

Kadish A., Spear J., Levine J., Hanich R., Prood C., Moore E.N. (1986) "Vector Mapping of Myocardial Activation", Circulation. vol. 74, No. 3: 603–615.

Primary Examiner—Marvin M. Lateef
Assistant Examiner—Jeoyuh Lin
(74) Attorney, Agent, or Firm—Paul A. Coletti

(57) ABSTRACT

A method of reconstructing a map of a volume, including determining coordinates of a plurality of locations on a surface of the volume having a configuration, generating a grid of points defining a reconstruction surface in 3D space in proximity to the determined locations, for each of the points on the grid, defining a respective vector, dependent on a displacement between one or more of the points on the grid and one or more of the locations, and adjusting the reconstruction surface by moving substantially each of the points on the grid responsive to the respective vector, so that the reconstruction surface is deformed to resemble the configuration of the surface.

22 Claims, 12 Drawing Sheets

U.S. PATENT DOCUMENTS

| | | | |
|---|---|---|---|
| 5,293,869 | 3/1994 | Edwards et al. | 128/642 |
| 5,297,549 | 3/1994 | Beatty et al. | 128/642 |
| 5,311,866 | 5/1994 | Kagan et al. | 128/642 |
| 5,313,943 | 5/1994 | Houser et al. | 128/642 |
| 5,324,284 | 6/1994 | Imran | 606/15 |
| 5,341,807 | 8/1994 | Nardella | 128/642 |
| 5,345,936 | 9/1994 | Pomeranz et al. | 128/642 |
| 5,383,917 | 1/1995 | Desai et al. | 607/702 |
| 5,433,198 | 7/1995 | Desai | 128/642 |
| 5,454,370 | 10/1995 | Avitall | 128/642 |
| 5,458,116 | 10/1995 | Egler | 128/710 |
| 5,485,849 | 1/1996 | Panescu et al. | 128/699 |
| 5,487,391 | 1/1996 | Panescu | 128/699 |
| 5,489,782 * | 2/1996 | Wernikoff | 250/369 |
| 5,549,109 | 8/1996 | Samson et al. | 128/642 |
| 5,595,183 | 1/1997 | Swanson et al. | 128/697 |
| 5,601,084 * | 2/1997 | Sheehan et al. | 128/661.04 |
| 5,637,090 | 6/1997 | McGee et al. | 604/95 |
| 5,640,967 | 6/1997 | Fine et al. | 128/710 |
| 5,657,755 | 8/1997 | Desai | 128/642 |
| 5,687,737 * | 11/1997 | Branham et al. | 600/523 |
| 5,697,377 | 12/1997 | Wittkampf | 128/696 |
| 5,718,241 | 2/1998 | Ben-Haim et al. | 128/702 |
| 5,730,704 | 3/1998 | Avitall | 600/374 |
| 5,755,664 | 5/1998 | Rubenstein | 600/377 |
| 5,782,773 | 7/1998 | Kuo et al. | 600/523 |
| 5,803,084 | 9/1998 | Olson | 128/699 |
| 5,812,691 * | 9/1998 | Udupa et al. | 382/128 |
| 5,820,568 | 10/1998 | Willis | 600/523 |
| 5,830,150 | 11/1998 | Palmer et al. | 600/523 |
| 5,842,984 | 12/1998 | Avitall | 600/374 |
| 5,889,524 | 3/1999 | Sheehan et al. | 345/419 |
| 5,951,485 | 9/1999 | Cyrus et al. | 600/523 |

* cited by examiner

THREE-DIMENSIONAL RECONSTRUCTION OF INTRABODY ORGANS

FIELD OF THE INVENTION

The present invention relates generally to systems and methods for mapping, and specifically to methods of mapping of intrabody organs.

BACKGROUND OF THE INVENTION

Cardiac mapping is used to locate aberrant electrical pathways and currents within the heart, as well as mechanical and other aspects of cardiac activity. Various methods and devices have been described for mapping the heart. Such methods and device are described, for example, in U.S. Pat. Nos. 5,471,982 and 5,391,199 and in PCT patent publications WO94/06349, WO96/05768 and WO97/24981. U.S. Pat. No. 5,391,199, for example, describes a catheter including both electrodes for sensing cardiac electrical activity and miniature coils for determining the position of the catheter relative to an externally-applied magnetic field. Using this catheter a cardiologist may collect a set of sampled points within a short period of time, by determining the electrical activity at a plurality of locations and determining the spatial coordinates of the locations.

In order to allow the surgeon to appreciate the determined data, a map, preferably a three dimensional (3D) map, including the sampled points is produced. U.S. Pat. No. 5,391,199 suggests superimposing the map on an image of the heart. The positions of the locations are determined with respect to a frame of reference of the image. However, it is not always desirable to acquire an image, nor is it generally possible to acquire an image in which the positions of the locations can be found with sufficient accuracy.

Various methods are known in the art for reconstructing a 3D map of a cavity or volume using the known position coordinates of a plurality of locations on the surface of the cavity or volume. Some methods include triangulation, in which the map is formed of a plurality of triangles which connect the sampled points. In some cases a convex hull or an alpha-hull of the points is constructed to form the mesh, and thereafter the constructed mesh is shrunk down to fit on the sampled points within the hull. Triangulation methods do not provide a smooth surface and therefore require additional stages of smoothing.

Another method which has been suggested is forming a bounding ellipsoid which encloses the sampled points. The sampled points are projected onto the ellipsoid, and the projected points are connected by a triangulation method. The triangles are thereafter moved with the sampled points back to their original locations, forming a crude piecewise linear approximation of the sampled surface. However, this method may reconstruct only surfaces which have a star shape, i.e., a straight line connecting a center of the reconstructed mesh to any point on the surface does not intersect the surface. In most cases heart chambers do not have a star shape.

In addition, reconstruction methods known in the art require a relatively large number of sampled locations to achieve a suitable reconstructed map. These methods were developed, for example, to work with CT and MRI imaging systems which provide large numbers of points, and therefore generally work properly only on large numbers of points. In contrast, determining the data at the locations using an invasive catheter is a time-consuming process which should be kept as short as possible, especially when dealing with a human heart. Therefore, reconstruction methods which require a large number of determined locations are not suitable.

SUMMARY OF THE INVENTION

It is an object of the present invention to provide an improved method for creating a map of a 3D volume or cavity, based on the positions of points on a surface of the volume or cavity.

It is an object of some aspects of the present invention to provide methods and apparatus for generating a map of a volume in the human body from a plurality of sampled points, regardless of the shape of the volume.

It is another object of some aspects of the present invention to provide a simple, rapid method for reconstructing a 3D map of a volume in the human body from a plurality of sampled points, preferably using fewer sampled points than is feasible using methods known the art.

It is another object of preferred embodiments of the present invention to provide a method for reconstructing a 3D map of a volume in the human body from a plurality of sampled points, assuming any topological relationship between the points.

It is another object of some aspects of the present invention to provide a simple method for reconstructing a 3D map of a volume in movement.

It is another object of some aspects of the present invention to provide a simple method for reconstructing a 3D map of a volume in the human body from a plurality of sampled points independent of the sampling order.

It is another object of some aspects of the present invention to provide a quick method for reconstructing a 3D map of a volume in the human body from a plurality of sampled points, such that the method may be used in interactive procedures.

It is another object of some aspects of the present invention to provide a method for reconstructing a smooth 3D map of a volume in the human body from a plurality of sampled points.

In preferred embodiments of the present invention, a processor reconstructs a 3D map of a volume or cavity in a patient's body (hereinafter referred to as the volume), from a plurality of sampled points on the volume whose position coordinates have been determined. In contrast to prior art reconstruction methods in which a large number of sampled points are used, the preferred embodiments of the present invention are directed to reconstruction of a surface based on a limited number of sampled points. The number of sampled points is generally less than 200 points and may be less than 50 points. Preferably, ten to twenty sampled points are sufficient in order to perform a preliminary reconstruction of the surface to a satisfactory quality.

An initial, generally arbitrary, closed 3D curved surface (also referred to herein for brevity as a curve) is defined in a reconstruction space in the volume of the sampled points. The closed curve is roughly adjusted to a shape which resembles a reconstruction of the sampled points. Thereafter, a flexible matching stage is preferably repeatedly performed once or more to bring the closed curve to accurately resemble the shape of the actual volume being reconstructed. Preferably, the 3D surface is rendered to a video display or other screen for viewing by a physician or other user of the map.

In preferred embodiments of the present invention, the initial closed curved surface encompasses substantially all the sampled points or is interior to substantially all the sampled points. However, it is noted that any curve in the vicinity of the sampled points is suitable. Preferably, the closed 3D curved surface comprises an ellipsoid, or any other simple closed curve. Alternatively, a non-closed curve may be used, for example, when it is desired to reconstruct a single wall rather than the entire volume.

A grid of a desired density is defined on the curve, and adjustment of the curve is performed by adjusting the grid points. The grid preferably divides the curved surface into quadrilaterals or any other polygons such that the grid evenly defines points on the curve. Preferably, the grid density is sufficient such that there are generally more grid points than sampled points in any arbitrary vicinity. Further preferably, the grid density is adjustable according to a desired compromise between reconstruction accuracy and speed.

In some preferred embodiments of the present invention, external information is used to choose an initial closed curve which is more closely related to the reconstructed volume, for example, using the image of the volume, as described above. Thus, the reconstruction procedure may produce a more accurate reconstruction in less time. Alternatively or additionally, a database of closed curves suitable for various volumes of the body is stored in a memory, and the curve to be used is chosen according to the specific procedure. In a further preferred embodiment of the present invention, a map of a reconstructed volume in a patient is used as a beginning curve for subsequent mapping procedures performed at later times on the same volume.

Preferably, the rough adjustment of the closed curve is performed in a single iteration, most preferably by calculating for each grid point an adjustment point, and moving the grid point a fraction of the distance to the adjustment point. Preferably, the grid point is moved about 50–80% of the distance between its original point and the adjustment point, more preferably about 75%.

The adjustment point is preferably determined by taking a weighted sum over substantially all the sampled points. Preferably, the weights are inversely related to the distances from the adjusted grid point to the sampled points, referred to herein as grid distances. In a preferred embodiment of the present invention, each weight is defined as the reciprocal of the sum of a small constant plus the grid distance, raised to a predetermined power, so that sampled points close to the grid point are given a larger weight. Preferably, the power is approximately between 4 to 9, most preferably 8. The small constant is preferably smaller than the magnitude of the smallest grid distance, and is preferably of the size of the accuracy of the determination of the coordinates of the sampled points. The small constant is used to prevent division by zero when a grid-point is on a sampled point.

In some preferred embodiments of the present invention, the weights also include a factor which is indicative of the density of points in the vicinity of their corresponding point. Preferably, the weight is multiplied by a density value between zero and one, indicative of the density, such that isolated sampled points influence the sum more than sampled points in a dense area. Preferably, the influence of the points is thus substantially independent of the density of points in their vicinity.

In a preferred embodiment of the present invention, the flexible matching step is performed by associating each sampled point with a corresponding grid-point, such that each sampled point is associated with the grid point which is closest to it. A movement vector is calculated for each of the associated and non-associated grid points. Preferably, the movement vectors are calculated based on vectors from the associated grid points to their respective sampled points. Further preferably, the sampled points influence the value of the movement vector for a specific point according to their proximity to the specific point. In addition, the function by which the movement vectors are calculated is preferably smooth and does not include complicated calculations. Preferably, the function is a weighted sum of the vectors from the associated grid points to their respective sampled points. The grid points are then moved according to their respective movement vectors.

Additionally or alternatively, the associated grid points are moved toward their corresponding sampled points by a percentage of the distance between them. Those grid points which are not associated with a sampled point are moved a distance which is determined by interpolation between the distances which surrounding points on the grid are moved. Preferably, the resulting grid is smoothed using a suitable smoothing transformation. Preferably, the process of associating and moving is repeated two or more times to allow finer adjustment of the closed curve.

In a preferred embodiment of the present invention, a user can adjust the number of times the flexible matching step is repeated according to a desired compromise between image quality and speed. Alternatively or additionally, a quick reconstruction is first provided to the user, and thereafter the calculation is repeated to receive a finer reconstruction. Preferably, the weights of the weighted sum used in the flexible matching stage are adjusted according to the number of times the matching is to be performed. Alternatively or additionally, the weights are determined for each flexible matching step according to its place in the sequential order of the flexible matching steps.

Preferably, the distances used for the weights and/or for interpolation are Euclidean geometrical dins between the points. The Euclidean distance is easily computed and causes points on opposite walls of the volume to mutually repel, so that the walls do not intersect. Alternatively, other distances, such as the distance along the original or adjusted grid, may be used. In a preferred embodiment of the present invention, during the first flexible matching step the distance used is the distance along the original grid while subsequent flexible matching steps use the Euclidean distance.

In some preferred embodiments of the present invention, a smoothing process is applied to the reconstructed surface, preferably by applying a surface convolution with a Gaussian-like kernel. The smoothing process provides a better approximation of the surface and allows easier performance of calculations based on the reconstructed surface. However, applying the surface convolution results in some shrinkage of the surface, and therefore an affine transformation is preferably performed on the smoothed surface. The affine transformation is preferably chosen according to those sampled points which are external to the reconstructed surface. The chosen affine transformation preferably minimizes the mean square distance of the eternal points to the surface.

Preferably, when the reconstruction is finished, each sampled point substantially coincides with a grid point. In some preferred embodiments of the present invention, a final exact matching stage is performed. Each sampled point is associated with a closest grid point, and the associated grid point is moved onto the sampled point. The rest of the grid points are preferably not moved. Generally, most of the sampled points are by this stage very close to the reconstructed surface, and therefore the smoothness of the surface is substantially not affected. However, some outlier sampled points, i.e., sampled points which do not belong to the surface, may cause substantial changes to the surface. Preferably, the user may determine whether to move the surface onto points that are distanced from the surface by more than a predetermined maximum distance. Alternatively or additionally, the entire exact matching step is optional and is applied only according to a user request.

Further alternatively or additionally, the grid points are brought to a fixed distance from the sampled points. Leaving such a fixed distance may be desired, for example, when the sampled coordinates are of locations close to a distal tip of a sampling catheter rather than at the distal tip itself.

In preferred embodiments of the present invention, data regarding the sampled points are acquired by positioning a catheter within the volume which is to be reconstructed, for example, within a chamber of the heart. The catheter is positioned with a distal end thereof in contact with each of the sampled points in turn, and the coordinates of the points and, optionally, values of one or more physiological parameters are sensed at a distal end of the catheter. Preferably, the catheter comprises a coordinate sensor dose to its distal end, which outputs signals indicative of the coordinates of the tip of the catheter. Preferably, the coordinate sensor determines the position by transmitting and receiving electromagnetic waves, as described, for example, in PCT publications GB93/01736, WO94/04938, WO97/24983 and WO96/05768, or in U.S. Pat. No. 5,391,199, commonly owned by the present assignee and which are all incorporated herein by reference.

In some preferred embodiments of the present invention, the reconstructed volume is in movement, for example, due to beating of the heart. In such embodiments, the sampled points are preferably registered with a reference frame fixed to the heart. Preferably, a reference catheter is fixed in the heart, and the sampled points are determined together with the position of the reference catheter which is used to register the points, as described, for example, in the above-mentioned U.S. Pat. No. 5,391,199 and PCT publication WO96/05768.

Alternatively or additionally, when at least part of the movement is a cyclic movement, as in the heart, acquisition of the sampled points is synchronized to as specific time point of the cycle. Preferably, when the sampled volume is in the heart, an ECG signal is received and is used to synchronize the acquisition of the sampled points. For example, the sampled points may be acquired at end diastole. Further alternatively or additionally, the coordinates of each of the sampled points are determined together with an indication of the time point relative to the cyclic movement in which the coordinates were acquired. Preferably, the indication includes the relative time from the beginning of the cycle and the frequency of the cyclic movement. According to the frequency and the relative time, the determined coordinates are corrected to end diastole, or any other point in the cyclic movement.

In some preferred embodiments of the present invention, for each sampled point a plurality of coordinates are determined at different time points of the cyclic movement. In one of these preferred embodiments, each sampled point has two coordinates which define the range of movement of the point. Preferably, if the plurality of coordinates of different points are associated with different cycle frequencies, the coordinates are transformed so as to correspond to a set of coordinates in a single-frequency cyclic movement. Further preferably, the coordinates are processed so as to reduce or substantially eliminate any contribution due to movement other than the specific (cardiac) cyclic movement, such as movement of the chest due to respiration. Reconstruction is performed for a plurality of configurations of the volume at different time points of the cyclic movement. Preferably, a first reconstruction is performed as described above to form an anchor reconstruction surface, and reconstruction of surfaces for other time points of the cycle are performed relative to the anchor reconstruction surface.

Preferably, for each further time point of the cyclic movement, the anchor surface is adjusted according to the coordinates of the sampled points at the further time point relative to the coordinates of the sampled points of the anchor surface Preferably, the anchor surface is adjusted by a quadratic transformation which minimizes a mean square error, the error representing the distances between the sampled points of the further time point and the adjusted surface. Alternatively or additionally, an affine transformation is used instead of the quadratic transformation Further alternatively or additionally, a simple transformation is used for surfaces having relatively few sampled points, while surfaces with a relatively large number of sampled points a quadratic transformation is used. The simple transformation may be an affine transformation, a scaling and rotation transformation, a rotation transformation, or any other suitable transformation.

Preferably, the adjustment of the surface for the further time points includes, after the transformation, one or more, preferably two, flexible matching steps and/or an exact matching stage.

Alternatively or additionally, the reconstruction is performed separately for each of the further time points. Further alternatively or additionally, a first reconstruction of the surfaces for the further time points is performed relative to the anchor surface, and afterwards a more accurate reconstructed is performed for each time point independently.

In some preferred embodiments of the present invention, dedicated graphics hardware which is designed to manipulate polygons is used to perform the reconstruction stages described above.

In some preferred embodiments of the present invention, one or more physiological parameters are acquired at each sampled point. The physiological parameters for the heart may comprise a measure of cardiac electrical activity, for example, and/or may comprise any other type of local information relating to the heart, as described in the PCT patent publication WO97/24981, also owned by the present assignee and further incorporated herein by reference. The one or more physiological parameters may be either scalars or vectors and may comprise, for example, a voltage, temperature, pressure, or any other desired value.

Preferably, after the volume is reconstructed based on the coordinates, values of the physiological parameter are determined for each of the grid points based on interpolation of the parameter value at surrounding sampled points. Preferably, the interpolation of the physiological parameter is performed in a manner proportional to the aggregate interpolation of the coordinates. Alternatively, the physiological parameters are interpolated according to the geometrical distance between the points on the grid. Alternatively or additionally, the physiological parameters are interpolated in a manner similar to the flexible matching step described hereinabove.

The reconstructed surface may be displayed in movement, and/or a physician may request a display of a specific time point of the cycle. Preferably, the physiological parameter is displayed on the reconstructed surface based on a predefined color scale. In a preferred embodiment of the present invention, the reliability of reconstruction of regions of the reconstructed surface is indicated on the displayed surface. Preferably, regions which are beneath a user-defined threshold are displayed as semi-transparent, using known methods such as α-blending. Preferably, the reliability at any grid point is determined according to its proximity to sampled points. Those points on the grid which are beyond a predetermined distance from the nearest sampled point are less reliable.

In some preferred embodiments of the present invention, acquired images such as LV-grams and fluoroscopic images are used together with the sampled points to enhance the speed and/or accuracy of the reconstruction. Preferably, the processor performs an object recognition procedure on the image to determine the shape of the closed 3D curved surface to use in constructing the initial grid of the reconstruction. Alternatively or additionally, the image is used by the physician to select areas in which it is most desired to receive sampled points.

In some preferred embodiments of the present invention, the physician may define points, lines, or areas on the grid which must remain fixed and are not to be adjusted. Alternatively or additionally, some points may be acquired as interior points which are not to be on the map since they are not on a surface of the volume. The reconstruction procedure is performed accordingly so that the closed curve is not moved too close to the interior points.

In some preferred embodiments of the present invention, the reconstruction surface is used to determine an accurate estimate of the volume of the cavity. The surface is divided by the grid points into quadrilaterals, and each quadrilateral is further divided into two triangles. Based on these triangles the volume defined by the surface is estimated. Alternatively, the volume is calculated using a volumetric representation. Other measurements, such as geodesic surface measurements on the surface, may also be performed using the reconstructed surface.

It is noted that some of the stages described above may be ignored in some preferred embodiments of the invention, in order to save processing time and speed up the reconstruction procedure.

There is therefore provided in accordance with a preferred embodiment of the present invention, a method of reconstructing a map of a volume, including determining coordinates of a plurality of locations on a surface of the volume having a configuration, generating a grid of points defining a reconstruction surface in 3D space in proximity to the determined locations, for each of the points on the grid, defining a respective vector, dependent on a displacement between one or more of the points on the grid and one or more of the locations, and adjusting the reconstruction surface by moving substantially each of the points on the grid responsive to the respective vector, so that the recession surface is deformed to resemble the configuration of the surface.

Preferably, the method includes displaying the reconstruction surface.

Preferably, generating the grid includes generating a grid such that the reconstruction surface encompasses substantially all of the determined locations or is interior to substantially all of the determined locations.

Preferably, generating the grid includes defining an ellipsoid.

Preferably, the reconstruction surface is defined and adjusted substantially independently of any assumption regarding a topology of the volume.

Further preferably, the reconstruction surface is defined and adjusted substantially without reference to any point within the volume.

Alternatively or additionally, generating the grid includes acquiring an image of the volume and defining the reconstruction surface such that it resembles the image of the volume.

Further alternatively or additionally, generating the grid includes choosing a grid from a memory library according to at least one characteristic of the volume.

Preferably, adjusting the surface includes a rough adjustment stage and a flexible matching stage.

Preferably, the rough adjustment stage includes moving each point on the grid toward a respective weighted center of mass of the determined locations, and locations closer to the point on the grid are given larger weight.

Preferably, moving each point in the rough adjustment stage includes defining, for each of the points on the grid, a respective rough adjustment vector which includes a weighted sum of vectors from the point to each of the determined locations and moving the points a distance proportional to the respective vector.

Preferably, defining the rough adjustment vector includes calculating a weight for each of the summed vectors that is generally inversely proportional to a magnitude of the summed vector raised to a predetermined power.

Preferably, the weight includes an inverse of a sum of a constant and the magnitude of the vector raised to a power between 4 and 10. Preferably, the constant is smaller than a precision of the location determination.

Preferably, moving each point includes moving each point toward a respective target point by a distance between 50 and 90% of the distance between the point and the target point.

Preferably, the flexible matching stage includes selecting a grid point to be associated respectively with each of the determined locations. Preferably, selecting the grid point includes finding for each determined location a point on the grid that is substantially closest thereto.

Further preferably, the flexible matching stage includes moving the selected grid points toward their respective determined locations.

Preferably, moving the selected grid points includes moving the grid points substantially onto their respective, determined locations.

Preferably, the flexible matching stage includes moving grid points that were not selected by an amount dependent on the movements of surrounding grid points.

Preferably, moving the grid points that were not selected includes moving the grid points by an amount dependent substantially only on the movements of surrounding selected grid points.

Preferably, moving the grid points includes calculating a movement of a grid point that was not selected based on the movements of the surrounding selected grid points and distances from these surrounding grid points.

Preferably, calculating the movement of the grid point includes interpolating between the movements of surrounding grid points.

Preferably, the distances include geometrical distances. Alternatively or additionally, the distances include a length of the reconstruction surface between the grid points.

Preferably, the flexible matching stage includes defining a displacement function which includes a weighted sum of vectors, each vector connecting a location and its associated point.

Preferably, the flexible matching stage includes moving the grid points according to the displacement function so as to smooth the surface.

Preferably, determining the coordinates includes positioning a catheter tip at the plurality of locations.

Preferably, positioning the catheter tip includes positioning the catheter at a plurality of locations in a chamber of the heart.

Preferably, determining the coordinates includes positioning a catheter tip at the plurality of locations.

Preferably, determining the coordinates includes transmitting and receiving noni4onizing waves.

Preferably, determining the coordinates includes positioning at the plurality of locations a device which generates signals indicative of the position of the device.

Preferably, the device generates signals indicative of the six degrees of position and orientation of the device.

Preferably, determining the coordinates includes receiving the coordinates from an external source.

Preferably, the method includes acquiring a signal indicative of a value of physiological activity at substantially each of the plurality of locations.

Preferably, acquiring the signal includes acquiring a signal indicative of a value of electrical activity at the location.

Preferably, the method includes estimating a value of the physiological activity at the adjusted grid points.

Preferably, estimating the value of the physiological activity includes estimating based on an acquired value of the physiological activity at a location in a vicinity of the adjusted grid points.

Preferably, estimating based on the acquired value includes interpolating the value responsive to deformation of the reconstruction surface.

Preferably, determining coordinates of a plurality of locations includes determining coordinates of less than 200 locations, more preferably of less than 50 locations, and most preferably of less than 20 locations.

Preferably, the volume is in motion, and determining the coordinates includes determining a correction factor responsive to the motion.

Preferably, the motion includes cyclic motion, and determining the correction factor includes determining a factor responsive to a cycle frequency of the motion.

Preferably, determining the factor includes filtering out motion at a frequency substantially different from the cycle frequency.

Preferably, the motion includes cyclic motion, and determining the coordinates includes determining the coordinates at a predetermined phase of the cyclic motion.

Preferably, determining the coordinates at the predetermined phase includes determining the coordinates in a plurality of time points and adjusting the coordinates relative to the cyclic movement.

Preferably, adjusting the coordinates includes determining a rate of the cyclic movement together with the coordinates for substantially each coordinate determination.

Preferably, generating the grid and adjusting the reconstruction surface are performed separately with respect to the coordinates determined in each phase of the cyclic motion.

Alternatively or additionally, generating and adjusting are performed for the coordinates of a plurality of phases of the cyclic motion so as to form a motion map of the volume.

Preferably, generating the grid and adjusting the reconstruction surface are performed for a first group of coordinates determined in a first phase of the cyclic motion, and the reconstructed surface of the first group is adjusted to form a reconstructed surface in one or more additional phases.

Preferably, the method includes smoothing the reconstructed surface.

Preferably, the method includes applying an affine transformation to the reconstructed surface.

Preferably, the method includes a final stage in which each determined location is associated with a respective grid point, and the associated grid points are moved onto the determined locations while non-associated grid points are substantially not moved.

Preferably, the method includes estimating a measure of the volume responsive to the reconstructed surface.

Preferably, estimating the measure of the volume includes choosing an arbitrary point inside the grid and calculating the volumes of tetrahedrons defined by the arbitrary point and groups of three points on the grid which cover the entire grid surface.

There is further provided in accordance with a preferred embodiment of the present invention, apparatus for reconstructing a map of a volume from coordinates of a plurality of determined locations on a surface of the volume having a configuration, including a processor, which receives the coordinates and generates a grid of points defining a reconstruction surface in 3D space in proximity to the determined locations, and which defines a respective vector for each of the points on the grid, dependent on a displacement between one or more of the points on the grid and one or more of the locations, and which adjusts the reconstruction surface by moving each of the points on the grid responsive to the respective vector, so that the reconstruction surface is deformed to resemble the configuration of the surface of the volume.

Preferably, the apparatus includes a display screen for displaying the adjusted surface.

Preferably, the processor analyzes the adjusted surface to determine a characteristic of the volume.

Preferably, the apparatus includes a memory for storing the adjusted surface.

Preferably, the grid initially encompasses substantially all of the determined locations.

Preferably, the apparatus includes an imaging device for acquiring an image of the volume, and the processor defines the grid initially such that it resembles the image of the volume.

Preferably, the apparatus includes a memory library induding a plurality of closed curves, and the processor defines the grid initially by choosing a closed curve from the memory library according to at least one characteristic of the volume.

Preferably, the processor generates and defines the reconstruction surface substantially independently of any assumption regarding a topology of the volume.

Preferably, the processor generates and defines the reconstruction surface substantially without reference to any point within the volume.

Preferably, the processor forms the adjusted grid in two stages: a rough adjustment stage and a flexible matching stage.

Preferably, in the rough adjustment stage, the processor moves each point on the grid toward a respective weighted center of mass of the determined locations, and locations closer to the point on the grid are given larger weight.

Preferably, the processor calculates the center of mass using a weight that is substantially proportional for each location to the inverse of the sum of a small constant and the distance between the point and the location raised to a power between 4 and 10.

Preferably, the constant is smaller than a precision of the location determination.

Preferably, in the flexible matching stage, the processor selects a respective grid point to associate with each of the determined locations.

Preferably, the selected grid point for each determined location includes a point on the grid that is closest to the location.

Preferably, in the flexible matching stage, the processor moves the selected grid points toward their respective, associated locations.

Preferably, the processor moves the selected grid points onto the associated locations Preferably, the processor moves non-selected grid points by an amount dependent on the movements of surrounding grid points.

Preferably, the amount of movement of the non-selected grid points is dependent on the movements of surrounding selected grid points.

Preferably, the amount of movement of each of non-selected grid points is calculated by the processor based on the distances from the surrounding selected grid points to the non-selected grid point.

Preferably, the amount of movement of the non-associated grid points is calculated by the processor based on an interpolation of the movements of surrounding selected grid points.

Preferably, the distances include geometrical distances. Preferably, the apparatus includes a probe, which is brought into engagement with the surface to determine the locations thereon.

Further preferably, the probe includes a position sensor which indicates the position of a tip of the probe.

Preferably, the sensor includes at least one coil.

Preferably, the sensor generates signals indicative of position and orientation of the sensor.

Alternatively or additionally, the probe includes a functional portion for acquiring a value of a physiological activity at the plurality of locations.

Preferably, the functional portion includes an electrode.

Preferably, the processor estimates a value of the physiological activity at the adjusted grid points.

Preferably, the processor estimates the value of the physiological activity based on the acquired values of the physiological activity at points surrounding the adjusted grid points.

Preferably, the processor estimates the value by interpolation from the acquired values responsive to deformation of the reconstruction surface.

Preferably, the apparatus includes a reference catheter for registering the determined locations relative to a frame of reference associated with the volume.

Preferably, the apparatus includes an ECG monitor for gating the operation of the probe so as to determine the points at a fixed phase of a cyclic movement of the volume.

There is further provided in accordance with a preferred embodiment of the present invention, a method of displaying values of a parameter which varies over a surface, including determining a value of the parameter at each of a plurality of points on the surface, and rendering an image of the surface to a display with a different degree of transparency in different areas of the surface, responsive in each of the areas to the value of the parameter at one or more points in the area.

Preferably, determining the value includes sampling a plurality of points and creating a map of the surface responsive thereto, and rendering the image includes rendering a graphic representation of the map.

Preferably, creating the map includes creating a three-dimensional map.

Preferably, determining the value includes determining a measure of reliability of the map in each of the areas.

Preferably, rendering the image includes rending one or more of the areas having a low measure of reliability relative to another one or more of the areas with a relatively greater degree of transparency.

Preferably, determining the measure of reliability includes determining a density of the sampled points.

Preferably, rendering the image includes defining a color scale and displaying a color associated with the value, at each of the plurality of points.

Preferably, the plurality of points includes sampled points and interpolated points, and determining the measure of reliability includes assigning a high reliability measure to the sampled points.

Preferably, determining the measure of reliability includes assigning measures of reliability to the interpolated points according to their respective distance from a closest sampled point.

BRIEF DESCRIPTION OF THE DRAWINGS

The present invention will be more fully understood from the following detailed description of the preferred embodiments thereof, taken together with the drawings in which.

DETAILED DESCRIPTION OF PREFERRED EMBODIMENTS

Figure 1:
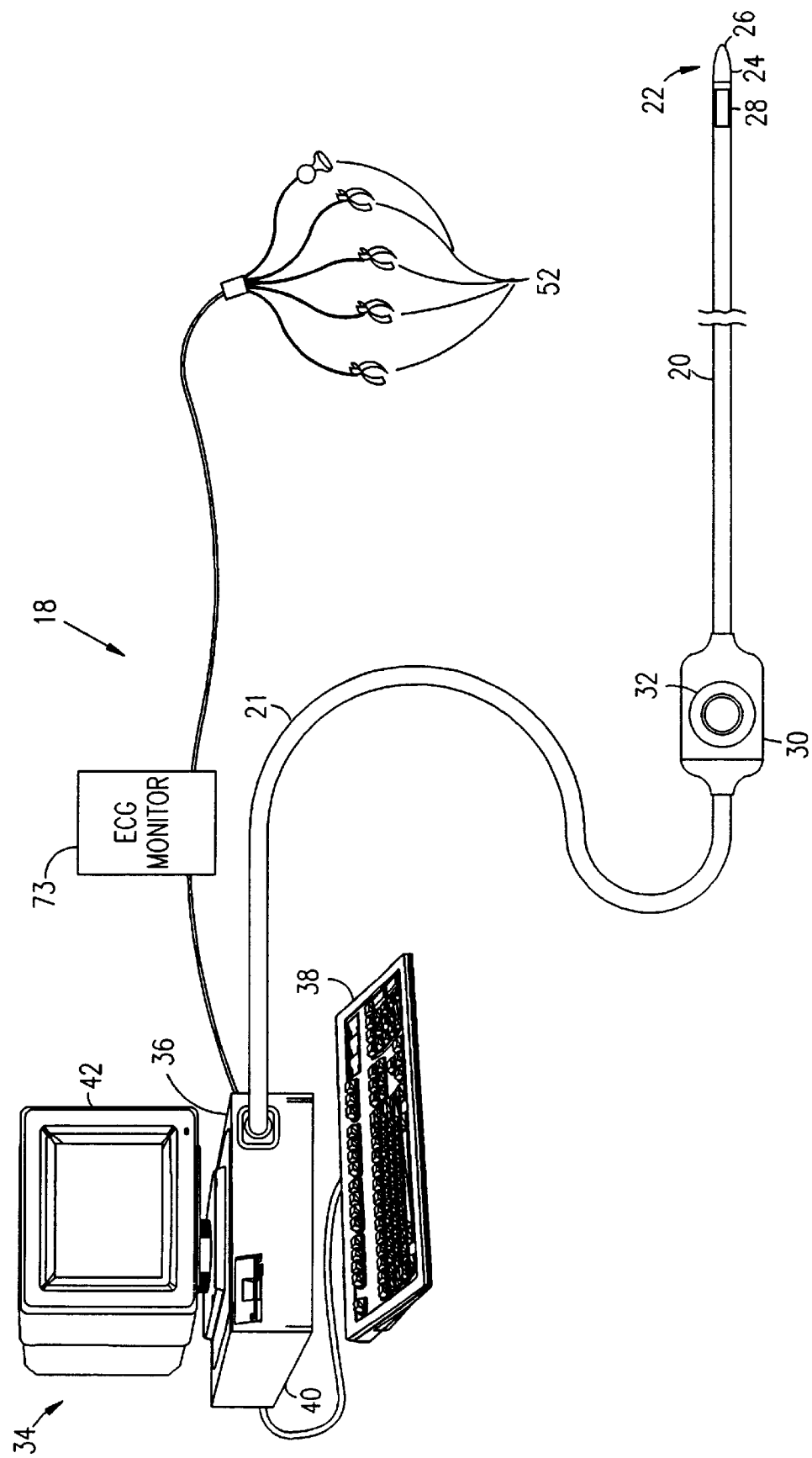
FIG. 1 is a schematic, perspective view of a heart mapping system, in accordance with a preferred embodiment of the present invention.

FIG. 1 shows a mapping system 18 for mapping of a volume in a patient's body, in accordance with a preferred embodiment of the present invention. System 18 comprises an elongate probe, preferably a catheter 20, for insertion into the human body. A distal end 22 of catheter 20 includes a functional portion 24 for performing diagnostic and/or therapeutic functions, adjacent to a distal tip 26. Functional portion 24 preferably comprises electrodes (not sown in the figure) for performing electrophysiological measurements, as described, for example, in U.S. Pat. No. 5,391,199 or in PCT publication WO97/24983, which are incorporated herein by reference. Alternatively or additionally, functional portion 24 may include other diagnostic apparatus for recording parameter values at points within the body. Such apparatus may include a chemical sensor, a temperature sensor, a pressure sensor and/or any other desired sensor. Functional portion 24 may determine for each point a single value of the parameter, or alternatively a plurality of values dependent on the time of their acquisition. Functional portion 24 may also include therapeutic apparatus, as is known in the art.

Distal end 22 of catheter 20 further includes a device 28 that generates signals used to determine the position and, preferably, orientation of the catheter within the body. Device 28 is preferably adjacent to functional portion 24, in a fixed relation with tip 26. Device 28 preferably comprises three non-concentric coils, such as described in PCT patent publication WO96/05768, whose disclosure is incorporated herein by reference. This device enables continuous generation of six dimensions of position and orientation information with respect to an externally-applied magnetic field. Alternatively, device 28 comprises other position and/or coordinate sensors as described in U.S. Pat. No. 5,391,199, U.S. Pat. No. 5,443,489 and PCT publication WO94/04938, which are incorporated herein by reference. Further alternatively or additionally, tip 26 is marked with a marker whose position can be determined from outside of the body, for example, a radio-opaque marker for use with a fluoroscope.

Catheter 20 preferably includes a handle 30, having controls 32 which are used by a surgeon to steer distal end 22 of the catheter in a desired direction, so as to position and/or orient it as desired. Catheter 20 preferably comprises a steering mechanism in distal end 22, as is known in the art, so that repositioning of tip 26 is facilitated.

Catheter 20 is coupled, via an extension cable 21, to a console 34 which enables the user to observe and regulate the functions of catheter 20. Console 34 preferably includes a computer 36, keyboard 38, signal processing circuits 40, which are typically inside the computer, and display 42. Signal processing circuits 40 typically receive, amplify, filter and digitize signals from catheter 20, including signals generated by position signal generating device 28, whereupon these digitized signals are received and used by computer 36 to compute the position and orientation of the catheter. Alternatively, appropriate circuitry may be associated with the catheter itself so that circuits 40 receive signals that are already amplified, filtered and/or digitized. Preferably, computer 36 includes a memory for storing positions and determined parameters of the points. Computer 36 preferably also includes dedicated graphic hardware for polygon manipulation, which allows performing reconstruction stages described hereinbelow using fast computer graphic techniques.

Preferably, system 18 also includes an ECG monitor 73, coupled to receive signals from one or more body surface electrodes 52 and to convey the signals to computer 36. Alternatively, the ECG monitoring function may be performed by circuits 40.

Figure 2:
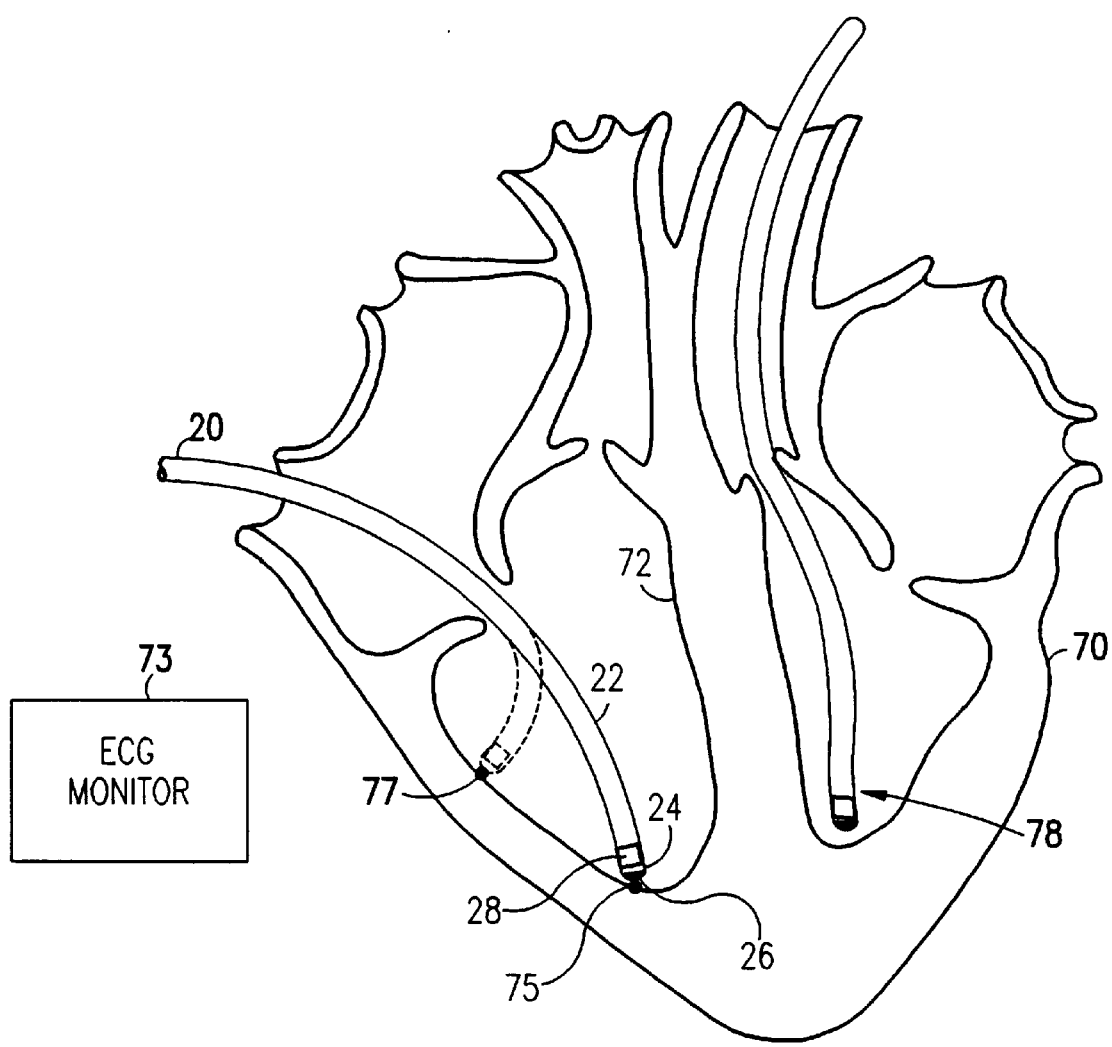
FIG. 2 shows a mapping catheter within a heart of a patient, in accordance with a preferred embodiment of the present invention.

FIG. 2 shows a distal portion of mapping catheter 20 within a heart 70 of a patient, in accordance with a preferred embodiment of the present invention. Catheter 20 is inserted into heart 70 and tip 26 is brought into contact with a plurality of locations, such as locations 75 and 77 on an inner surface 72 of heart 70. Surface 72 bounds the volume to be reconstructed, and it is locations on this surface which are to be sampled. At each of the plurality of locations, the coordinates of tip 26 are determined by device 28, preferably together with physiological information determined by functional portion 24. The determined coordinates and, optionally, physiological information form a local data point. The local data points from a plurality of locations are used for producing a map of heart 70, or of a portion of the heart.

At least one reference catheter 78 is preferably inserted into heart 70 and is placed in a fixed position relative to the heart. By comparing the positions of catheters 20 and 78, the position of tip 26 is accurately determined relative to the heart, irrespective of heart motion. Alternatively, any other suitable method may be used to compensate for movement of heart 70.

Preferably, the coordinates of tip 26 at the plurality of locations are determined at a common time-point in the cardiac cycle, preferably at end-diastole. Alternatively or additionally, each determined position is recorded together with a time-point, preferably relative to a predetermined time-point in the cardiac cycle, and together with indication of the current heart rate. The relative time-point and the rate of the cycle are used to correct for the movement of the heart. Thus, it is possible to determine positions of a large number of points, simply, in a limited time period Further alternatively or additionally, the position of tip 26 is determined at each location at two or more time-points in the cardiac cycle, such that for each location, a range of positions are determined. Thus, a geometric map of the plurality of locations may comprise a plurality of "snapshots" of heart 70, each snapshot associated with a different phase of the cardiac cycle. The cardiac cycle is preferably determined using ECG monitor 73, according to physiological readings from functional portion 24, or according to movements of reference catheter 78. Preferably, each position is determined together with the heart rate at the time of determination. A frequency and phase shift transformation is preferably applied to the plurality of positions at each location to bring the positions to a state as if they were determined at common time-points with respect to a common predetermined heart rate.

Preferably, the transformation applied to the positions also serves to reduce or eliminate the effects of any movement of the heart that is not due to the cardiac cycle, particularly chest movement due to respiration or other movements of the patient. These effects are removed by defining a cyclic trajectory of the points associated with each location, and then filtering out of the trajectory frequencies of motion other than frequencies associated with the heart rate. Preferably, any frequencies whose corresponding wavelengths do not evenly divide the cardiac cycle length, as determined from the ECG, are filtered out. The result for each location is a modified trajectory, including a corrected end-diastolic point, which is then used in reconstructing the map of the heart, as described hereinbelow.

Preferably, at each location at which tip 26 is positioned, it is verified that catheter 20 is in contact with the surface, using any suitable method, for example, as described in PCT publication WO97/24981, which is incorporated herein by reference.

Figure 3:
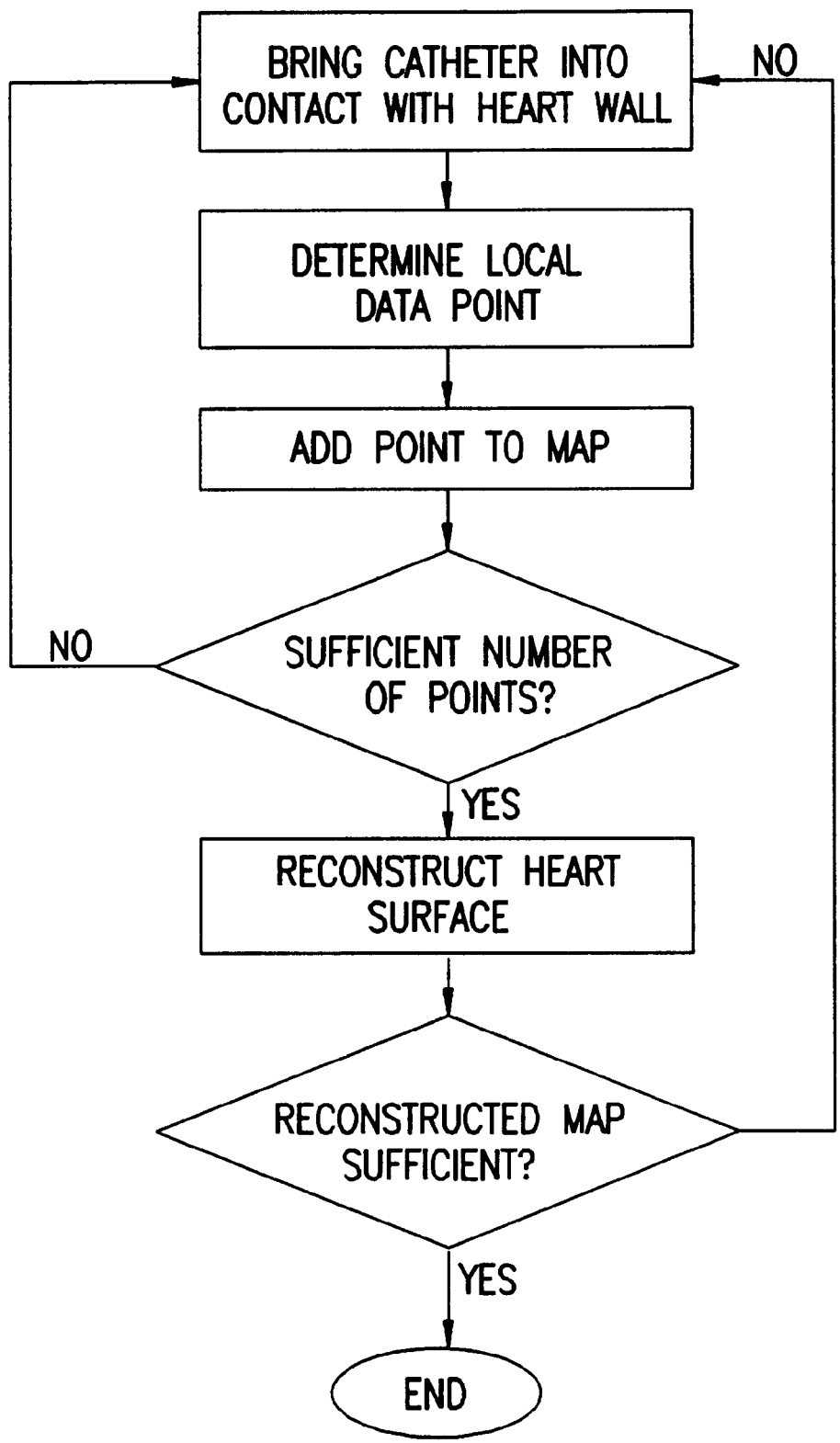
FIG. 3 is a flow chart illustrating a method of point sampling and map reconstruction, in accordance with a preferred embodiment of the present invention.

FIG. 3 is a flow chart illustrating the process of point sampling and reconstruction of a map, in accordance with a preferred embodiment of the present invention. As described above, catheter 20 is brought into contact with surface 72 of heart 70, and signals are received from the catheter to form a local data point characteristic of the location of tip 26. The local data point preferably includes coordinates of the point at a plurality of time points and one or more values, associated with the point, of at least one physiological parameter. Preferably, as mentioned above, the local data point includes an indication of the heart rate and time point in the heart cycle for each determined coordinate. The parameter values may be associated with specific time points or may be associated generally with the point.

Preferably, the contact between tip 26 and surface 72 is verified and the point is added to the map only if there is sufficient contact between the tip and the surface. In a preferred embodiment of the present invention, points for which proper contact does not exist are added to a database of interior points. These points are interior to the reconstructed surface and indicate areas on the map which are not part of the reconstructed surface. Alternatively or additionally, the user may indicate sampled points which are not to be used as part of the reconstructed surface, for example because they are outstandingly outside of the area of the other sampled points. Tip 26 is then moved to an additional location on surface 72 and data are likewise determined regarding the additional point. This procedure is repeated for a plurality of sampled points until data are determined for a sufficient number of points to make the map, or for a predetermined amount of time. Preferably, computer 36 counts the number of sampled points and compares the number of points to a predetermined required minimum number of points. Preferably, the predetermined number of points is between about ten to twenty points for fast procedures and is up to 100 points for longer procedures. Alternatively or additionally, the physician notifies computer 36 when a sufficient number of points have been sampled.

A map of heart 70 or of a volume within the heart is reconstructed, as described below, and the physician decides whether the map includes sufficient detail and appears to be accurate. If the map is not sufficient, more points are acquired and the map is accordingly updated or is again reconstructed. The reconstructed map is thereafter used for analysis of the functioning of heart 70, and the physician may decide on a required treatment accordingly.

Figure 4:
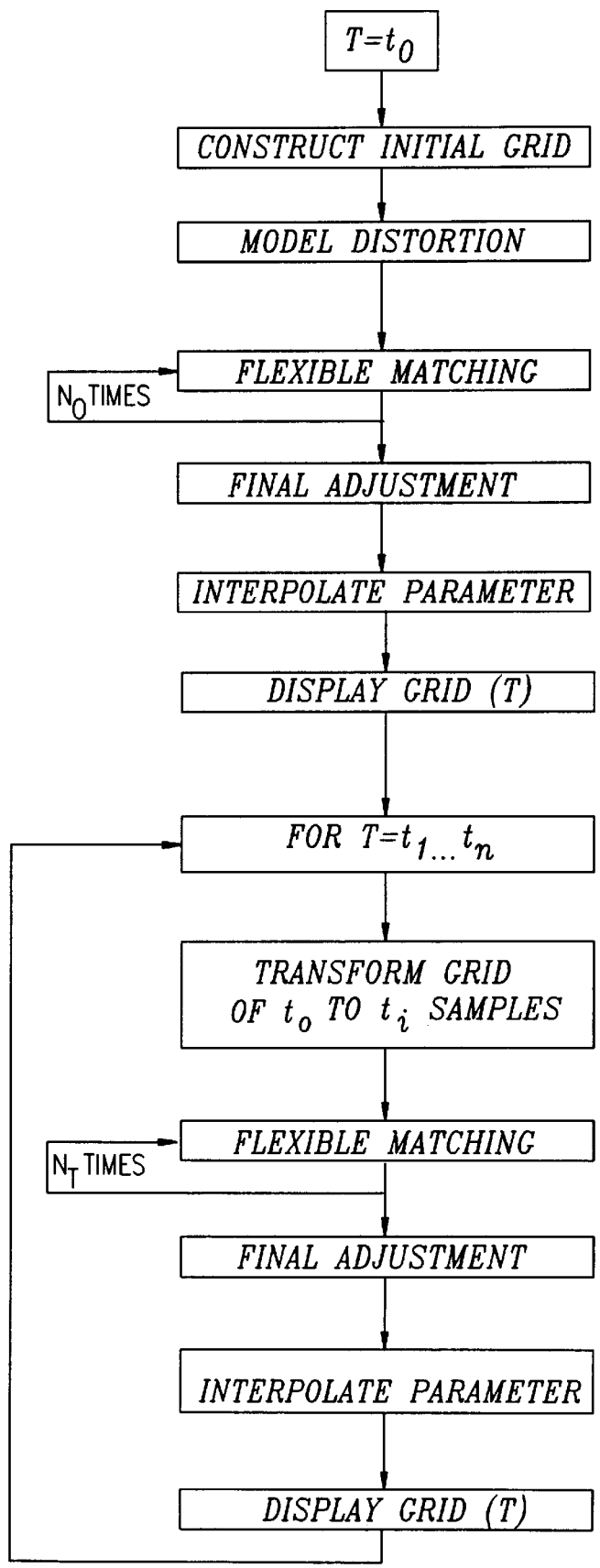
FIG. 4 is a flow chart illustrating a reconstruction procedure, in accordance with a preferred embodiment of the present invention.

FIG. 4 is a flow chart illustrating a reconstruction procedure, in accordance with a preferred embodiment of the present invention. Reconstruction is initially performed for positions determined at an anchor time point ($t_0$) of the heart cycle, such as end diastole. In a first stage of the initial reconstruction, a grid enclosing the sampled points is constructed. Thereafter, a stage of model distortion is applied to the grid, in which the grid is roughly adjusted to the shape defined by the sampled points. Subsequently, a preferably iterative stage of flexible matching is carried out finely adjusting the grid points according to the coordinates of the sampled points. Final adjustment is preferably applied to the grid including smoothing, an affine transformation and/or an exact matching stage which brings the grid to include substantially all the sampled points. The parameter values associated with the sampled points are preferably interpolated to all the grid points and the grid is subsequently displayed. This procedure is described in greater detail hereinbelow with reference to the figures that follow.

FIGS. 5A–5E are simplified, two dimensional graphs illustrating the reconstruction procedure for a single time-point, in accordance with a preferred embodiment of the present invention. For clarity of illustration, the figures and the following description refer to a simplified, two dimensional example. The extension of the principles illustrated herein to 3D reconstruction will be clear to those skilled in the art. Points $S_i$ are sampled points on the surface of the volume to be reconstructed, whose coordinates were received during the above-described sampling process.

Figure 5A:
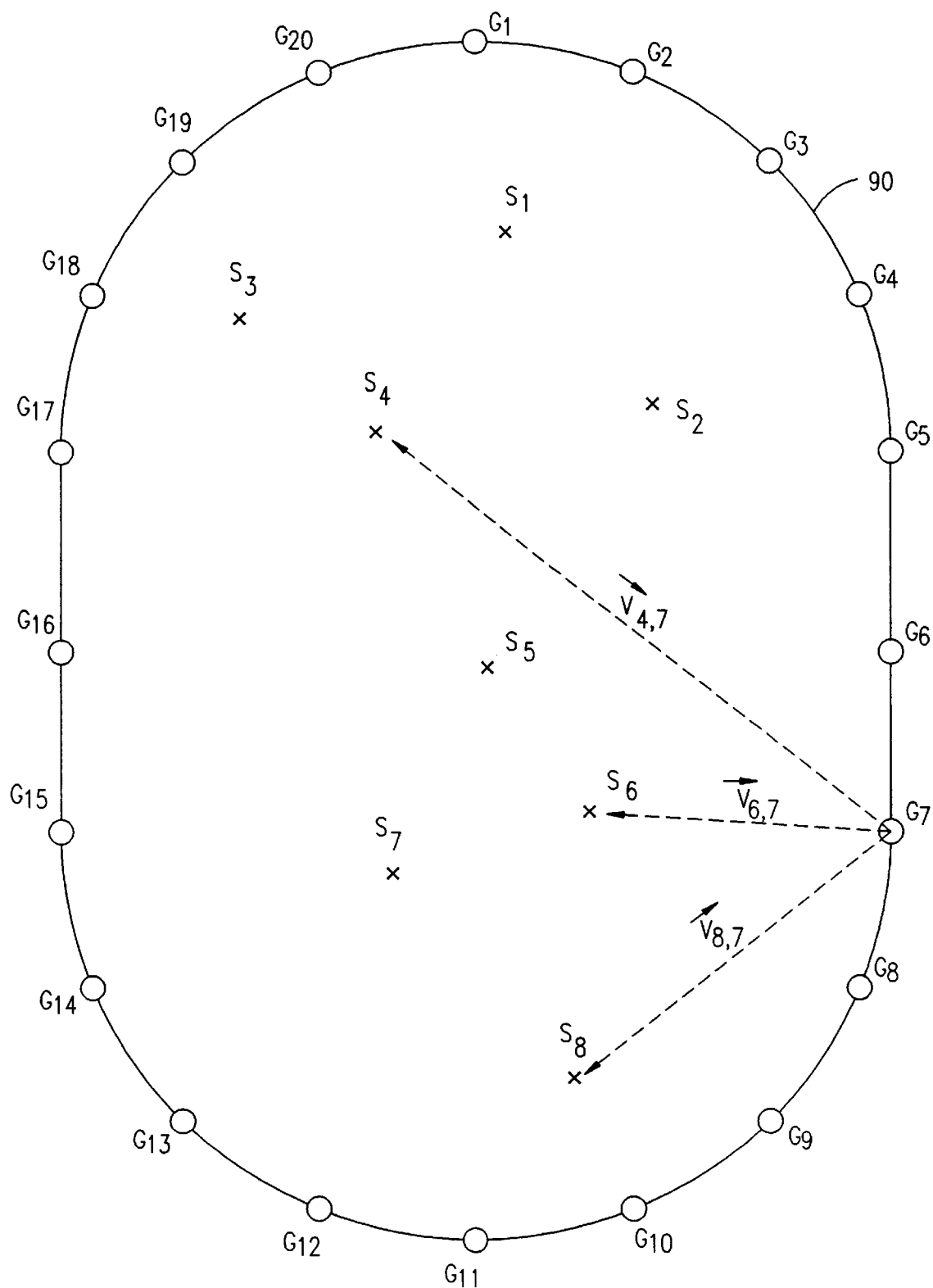
FIGS. 5A–5E are simplified, two dimensional graphs illustrating reconstruction of a map from sampled points, in accordance with a preferred embodiment of the present invention.

As shown in FIG. 5A, in the first stage, an initial grid 90 is defined in a vicinity of the sampled points, preferably enclosing the sampled points. Alternatively, grid 90 may be interior to the sampled points or pass between the points. Preferably, grid 90 comprises a number of points substantially greater than the number of sampled points. The density of the points is preferably sufficient to produce a map of sufficient accuracy for any required medical procedure. In a preferred embodiment of the present invention, the physician can adjust the density of points on the grid according to a desired compromise between reconstruction speed and accuracy. Preferably, grid 90 has an ellipsoidal shape or any other simple closed shape.

Alternatively or additionally, grid 90 has a shape based on known characteristics of the volume on whose surface the sampled points are located, for example, a shape determined by processing an LV-gram or other fluoroscopic or ultrasound image of the heart. In a preferred embodiment of the present invention, computer 36 contains a database of initial grids according to commonly-sampled volumes. The physician indicates, preferably via keyboard 38, which volume is being sampled and initial grid 90 is chosen accordingly. The chosen grid may be initially aligned with the sample points using any method known in the art, for example as described in Paul J. Besl and Neil D. McKay, "A method for registration of 3-D shapes," IEEE Transactions on Pattern Analysis and Machine Intelligence, 14(2):239–258, February 1992, which is incorporated herein by reference. The initial grid may alternatively be chosen from the grid library using geometric hashing or alignment, as described, for example, in Haim J. Wolfson, "Model-based object recognition by geometric hashing," in: O. Faugeras, ed., Computer Vision-ECCV90 (First European Conference on Computer Vision, Atibes, France, Apr. 23–27, 1990), Springer, Berlin, 1990, 526–536, or in P. Huttenlocher and S. Ullman, "Recognizing solid objects by alignment with an image," International Journal of Computer Vision, 5: 195–212, 1990, which are incorporated herein by reference. After the initial alignment, the method of the present invention proceeds, preferably as shown in FIG. 4 and described further hereinbelow.

Figure 5B:
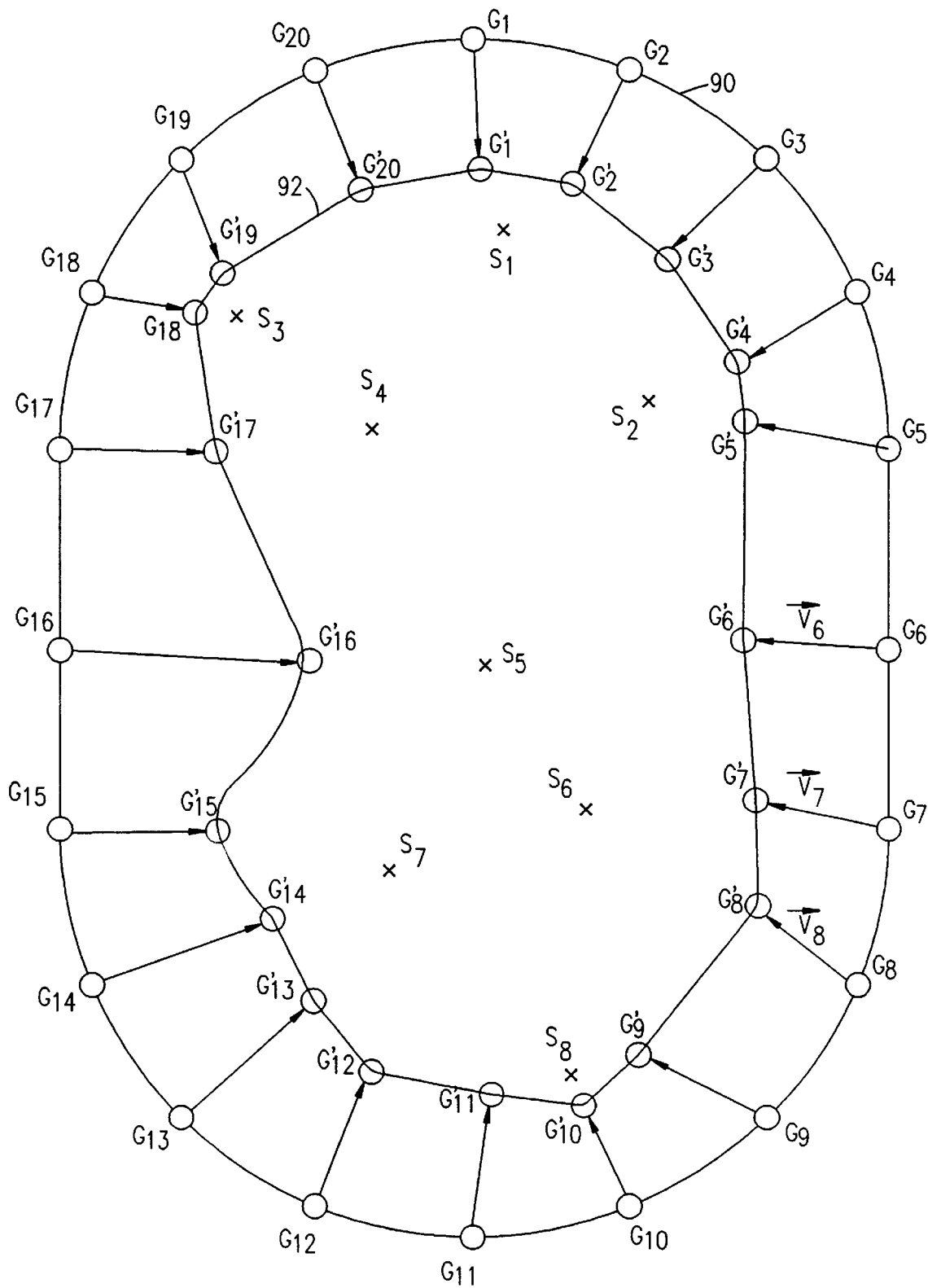

As shown in FIG. 5B, grid 90 is transformed to a grid 92 of points G', which is a rough adjustment toward the structure of the sampled volume. For each point Gj on grid 90, an adjustment vector $\vec{V}_j$ is constructed, and point Gj is replaced by a corresponding point Gj' on grid 92, which is displaced by $\vec{V}_j$ from point Gj on grid 90. Adjustment vector $\vec{V}_j$ is preferably a weighted sum of vectors $\vec{V}_{ji}$ from Gj to the sampled points $S_i$, as shown in FIG. 5A. Preferably, the weights of vectors $\vec{V}_{ji}$ in the sum are strongly inversely dependent on the magnitude of the vectors. Preferably, the weights are inversely dependent on the magnitude raised to a power (k), wherein k preferably ranges between 4 and 10, and is most preferably either between 6 and 8. In a preferred embodiment of the present invention, adjustment vectors $\vec{V}_j$ are calculated according to equation (1):

$$\vec{V}_j = C_f \sum_i \frac{\vec{V}_{ij}}{r_j^k + \varepsilon} \div \sum_i \frac{1}{r_j^k + \varepsilon}, r_j = |\vec{V}_{ij}| \qquad (1)$$

In equation (1), epsilon is a small scalar, preferably, smaller than the magnitude of the smallest vector which is not zero, and is preferably of the size of the accuracy of the determination of the sampled points, for example, about $10^{-6}$. Epsilon is used to prevent division by zero when the grid point is on a sampled point, and therefore the magnitude of the vector is zero. $C_f$ is a constant factor between 0.1 and 1, preferably between 0.5 and 0.9 most preferably about 0.75, which is adjusted to determine how closely the points $G_j'$ will approach points $S_i$ in the rough adjustment.

In a preferred embodiment, the influence of a sampled point Si on grid point Gj, takes into account not only the distance between the sampled point Si and Gj, as shown above in equation (1) but also the density of sampled points S in the vicinity of Si. Hence, the weighting factor applied to each sampled point, $$\frac{1}{r_j^6 + \varepsilon},$$

is multiplied by a density value $\square_i$, which preferably takes on values between 0 and 1. Preferably, $\delta_i$ is as defined in equation (2):

$$\delta_i = \frac{1}{\sum_j \frac{1}{(\|S_j - S_i\|^2 + 1)}} \qquad (2)$$

The more points there are in the vicinity of S, the smaller value $\delta$ takes on and the less influence each point has. Preferably, the sum of influences of a plurality of points in a close vicinity is the same as the influence of a single isolated point which preferably has a density value $\delta$ of about 1.

Figure 5C:
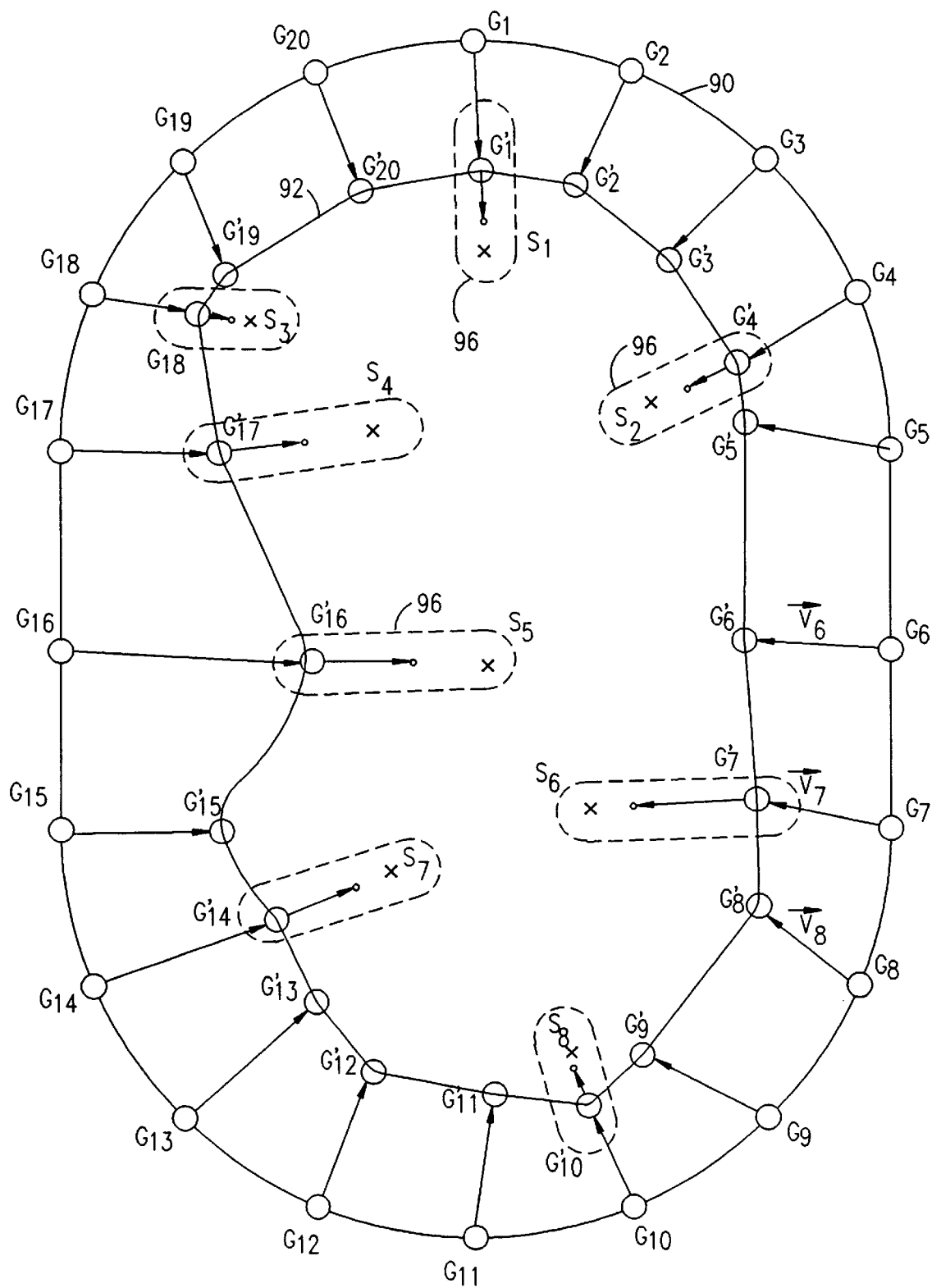

FIG. 5C illustrates a first part of a flexible matching step, in which each of sampled points $S_i$ is associated with a grid point Gj from roughly adjusted grid 92. The associated grid points are moved toward their respective sampled points, while the rest of the G' points on the roughly adjusted grid are moved according to interpolation of the movements of neighboring points on grid 92, as described further hereinbelow. Preferably, each sampled point $S_i$ is associated with the closest grid point. For example, the closest grid point to $S_1$ is $G_1'$, and these points are therefore associated. Preferably, computer 36 creates a memory list in which these pairs of points are listed. For clarity of this explanation, the associated points are marked by dashed ovals 96 in FIG. 5C.

Preferably, a transformation function f, which moves the associated grid points toward their respective sampled points, is generated. The non-associated grid points are also moved according to function f. Function f is preferably easily calculated, and transforms the grid to a smooth form. Preferably, function f is a weighted sum of the distances between the associated pairs of sampled and grid points, such that pairs of associated points close to the grid point influence its displacement more than pairs of associated points far from the grid point. Function f is preferably as given in equation (3) below, with $w_i(Gj)$ dependent on the distances between the grid point Gj and the associated grid points Gi, preferably as defined in equation (4). Alternatively, $w_i(Gj)$ is dependent on the distance between the grid point Gj and the sampled points Si, as in equation (1). In the flexible matching stage, k is preferably smaller than the power law in the rough adjustment stage in order to generate a smoother grid surface. Preferably, k in the flexible matching stage is between 2 and 6 and is most preferably 4. Preferably, k is an even number in order to simplify the calculations. Although the equations below are stated for convenience in scalar notation, it will be understood that $S_i$, $G_i$ and $f(G_j)$ are vector quantities, as in equation (1) above:

$$\vec{f}(G_j) = \frac{\sum_i w_i(G_j) \cdot (S_i - G_i)}{\sum w_i(G_j)} \qquad (3)$$

$$w_i(G_j) = \frac{1}{\|G_j - S_i\|^k + C} \quad C > 0 \qquad (4)$$

The constant C determines how close the associated grid points are moved toward their associated sampled points. For very small values of C, the associated grid points $G_i$ are moved substantially onto the sampled points $S_i$. Preferably, C is between 0.3 and 0.7, more preferably about 0.5. Alternatively or additionally, C is changed according to the number of times the flexible matching is to be performed. Further alternatively or additionally, in the first flexible matching step, C is relatively large, while in subsequent flexible matching steps C is gradually reduced.

The distance definition used in equations (2), (3) and (4) is preferably the Euclidean distance in $R^3$, due to its simplicity in calculation and the fact that it causes points on opposite walls of the reconstructed volume to repel one another.

In an alternative preferred embodiment of the present invention, the grid points which have an associated sampled point are moved toward their associated sampled points by a portion of the distance between them. Preferably, the points are moved a percentage of the distance between the associated pair. For example, in FIG. 5C the points are moved about ⅔ of the distance. Alternatively, the grid points are moved by any other amount dependent on the distance between the associated pair.

Figure 5D:
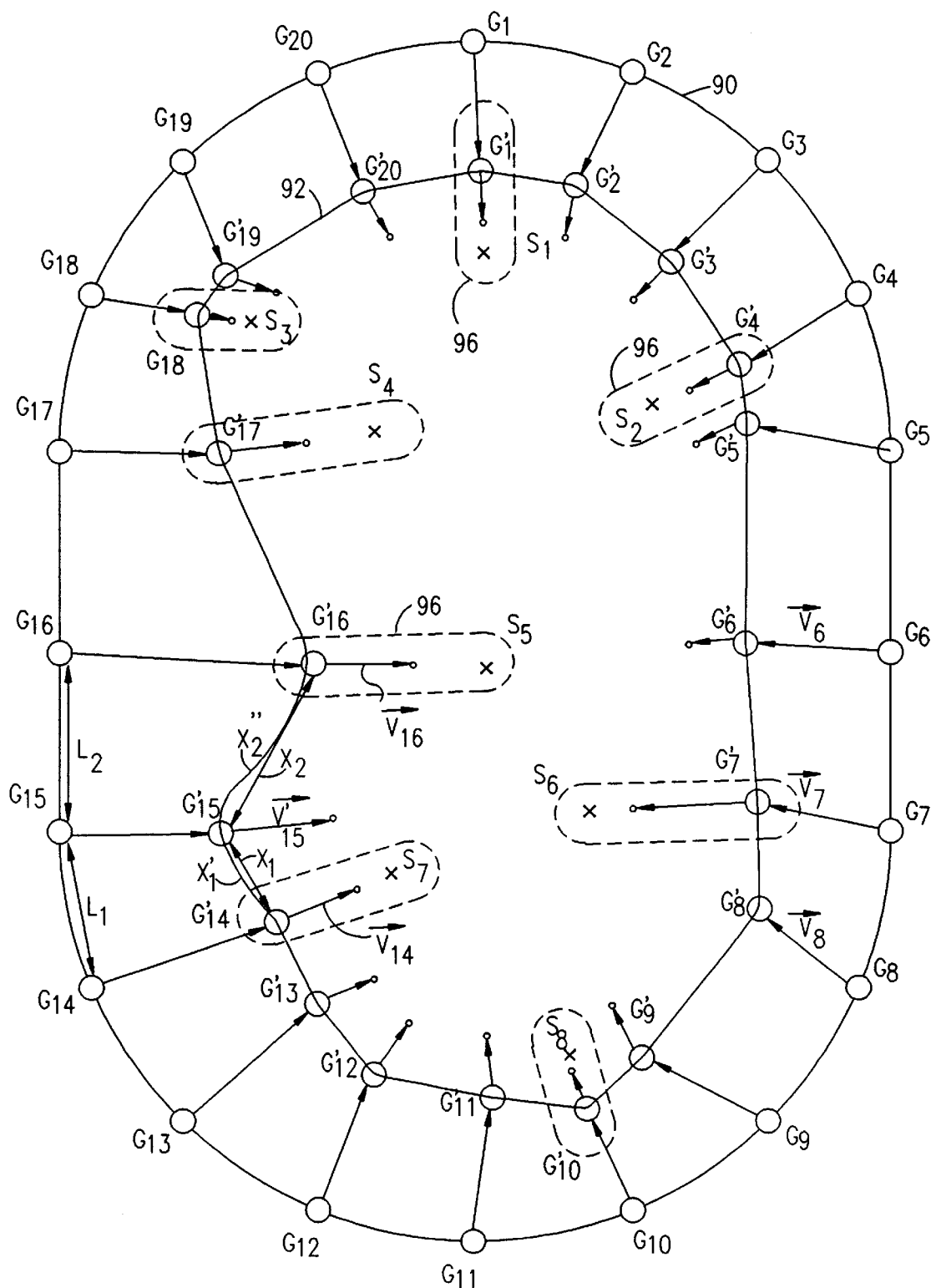

As shown in FIG. 5D, those grid points $G_k'$ which are not associated with sampled points $S_i$ are then moved according to a movement vector $\vec{V}_k$ which is dependent on the movements of the grid points $G_l'$ surrounding the point. Preferably, the non-associated points $G_k'$ are moved a distance which is a linear interpolation of the movements of the surrounding points $G_l'$. Preferably, the distance been the grid points is determined as the geometrical distance between the points as they are on the present adjusted grid. For example, the geometrical distance between $G_{15}'$ and $G_{16}'$ is indicated by $X_2$, and may be calculated according to the coordinates of the two points. Alternatively or additionally, the distance used is the grid-distance $\tilde{X}_2$ along the present adjusted grid, the grid-distance $\tilde{L}_2$ along the original grid, or the geometrical distance $L_2$ on the original grid. In a preferred embodiment of the present invention, in a first flexible matching step, the distance used is the grid-distance—either $l_2$ or $\tilde{X}_2$—while in subsequent flexible matching steps the distance used is the geometrical distance $X_2$.

For example, as shown in FIG. 5D, point $G_{15}'$ is moved a distance defined by a vector, which is a weighted sum of vectors $\vec{V}_{14}$, and $\vec{V}_{16}$ of grid points $G_{14}'$, and $G_{16}'$, respectively. Preferably, $\vec{V}_{15}$ is as described in equation (2) below, in which $d_1$ is a selected type of distance between $G_{15}$ and $G_{14}$, and may include $X_1, \bar{X}_1, l_1$ or any offer suitable distance definition. Likewise, $d_2$ is a selected type of distance between $G_{15}$ and $G_{16}$ and may include $X_2, \bar{X}_2, l_2$, or any other distance definition. Preferably, in the first flexible matching step illustrated in FIG. 5D, $d_1$ and $d_2$ are taken as $X_1$ and $X_2$ respectively.

$$\vec{V}'_{15} = \frac{d_2}{d_1+d_2}\vec{V}'_{14} + \frac{d_1}{d_1+d_2}\vec{V}'_{16} \qquad (5)$$

Although equation (8) illustrates a first-order linear interpolation, it will be understood that higher-order and non-linear interpolation methods may also be used.

Preferably, during the flexible matching stage, flexible matching steps are repeated a few times ($N_O$ times, as shown in FIG. 4). Each time, grid points are associated with the sampled points, and the associated and non-associated grid points are moved accordingly.

The rough adjustment and flexible matching tend to cause the grid to become non-uniform. Therefore, during a final adjustment stage the grid is preferably smoothed, for example, by applying a surface convolution with a Gaussian-like kernel. Preferably, the kernel is a 3×3 Gaussian kernel, and is applied to the grid a plurality of times, preferably between five and ten times. Alternatively, a larger kernel may be used in which case it may be applied to the grid fewer times, most preferably only once. The surface convolution, however, generally causes shrinkage of the surface, and therefore a simple transformation, preferably an affine transformation, is applied to the grid to cancel the shrinkage and improve the matching of the grid to the sampled points. The affine transformation is preferably chosen as the transformation which minimizes the mean square distance between sampled points outside of the grid and a surface defined by the grid. This choice of the transformation causes substantially all the sampled points to be on or inside the surface defined by the grid. This choice is in accordance with the anatomical structure of the heart in which outliers, i.e., points not on the sampled surface, are generally inside the sampled surface, i.e. inside a cardiac chamber rather than on the myocardial wall. Thus, the reconstructed grid is properly reconstructed by ignoring outliers which otherwise may deform the grid incorrectly.

To conclude the final adjustment stage, the user may optionally request an exact matching stage in which the grid surface is deformed to include substantially all the sampled points. Preferably, for each sampled point not on the grid surface as a result of prior stages, a closest grid point is chosen and moved to the position of the sampled point. The rest of the grid points are preferably not moved Preferably, internal points which are beyond a certain distance from the grid surface are not moved in this stage and are regarded as outliers. It is noted that external points are not generally distanced from the grid surface due to the affine transformation described above.

Figure 5E:
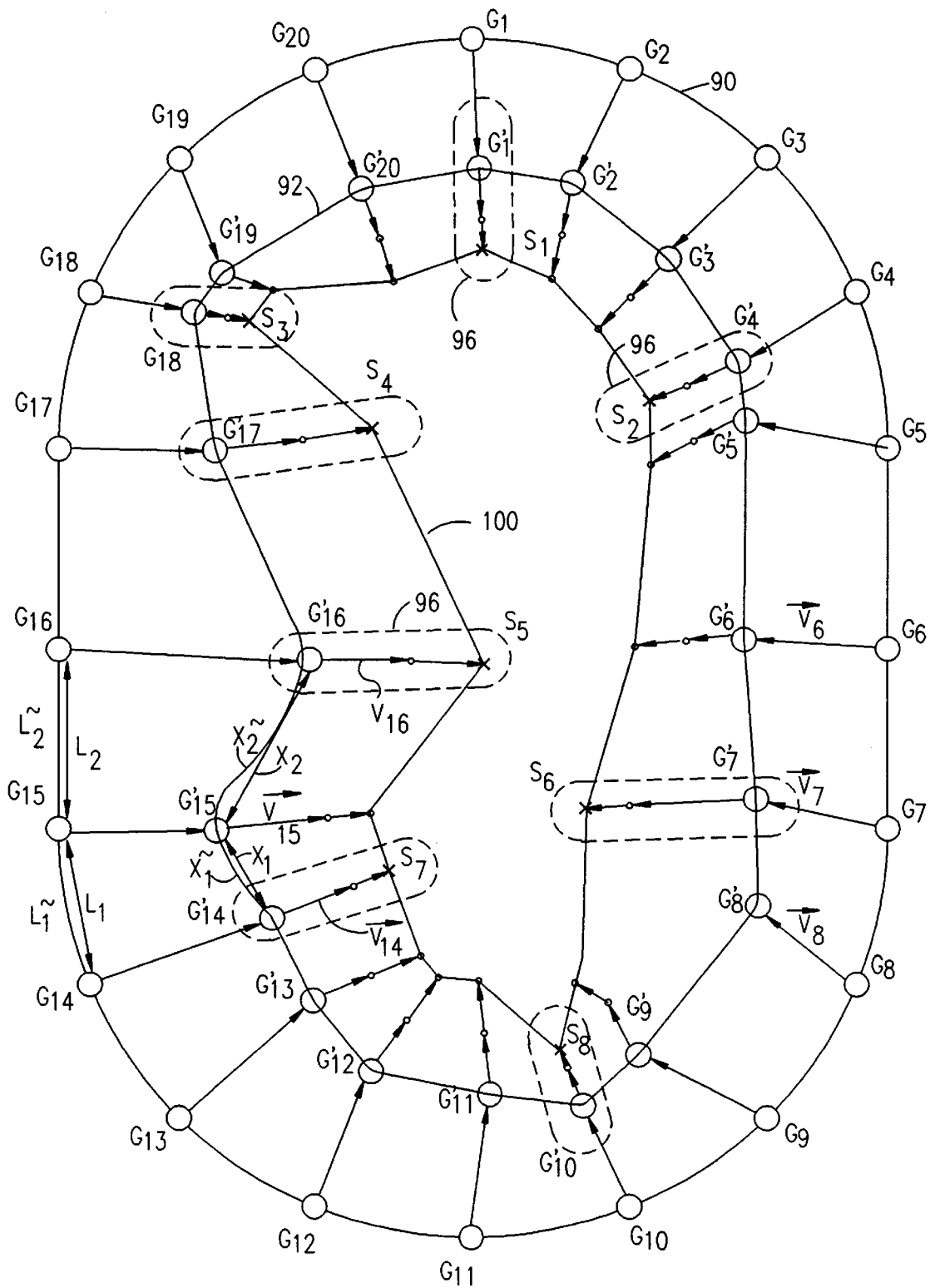

Alternatively or additionally, a last flexible matching step is performed in which the associated grid points are moved onto the sampled points, as shown in FIG. 5E. Curved line 100 in FIG. 5E represents the final grid configuration and comprises an accurate approximation of the sampled volume.

Alternatively, the flexible matching is performed in one step, and the associated points from the rough adjustment grid are immediately moved onto the sampled points. In a preferred embodiment of the present invention, computer 36 first produces an approximate map, in which the flexible matching is performed in one step. The approximate map is used by the physician to decide if more sampled points are needed. Once the physician decided that no more points are needed, computer 36 reconstructs a more accurate map in which the flexible matching is performed a plurality of times. Meanwhile, the physician may use the approximate map in order to save time. In further preferred embodiments, the first reconstructed map is produced with a relatively low density of points on the grid, while later reconstructions use a more dense grid.

Referring back to FIG. 4, when the sampled points include data from more than one time point, the reconstructed grid of the anchor time point (hereinafter referred to as the anchor grid) is preferably used to quickly reconstruct the grid for other time points $t_i$. For each of the other time points, a simple transformation is performed on the anchor grid to bring the grid close to the form of the sampled points of time $t_i$. The simple transformation is preferably a quadratic transformation or an affine transformation. Alternatively, the transformation comprises a rotation and/or scaling transformation. In some preferred embodiments of the present invention, the transformation is chosen according to the number of sampled points. Preferably, when there are a relatively large number of sampled points, a quadratic transformation is applied, while for fewer sampled points, simpler transformations are employed.

Flexible matching is then preferably performed on the transformed grid one or more times ($N_T$), preferably fewer times than were required in reconstruction of the anchor-time grid ($N_T > N_O$), most preferably twice. Final adjustments are then preferably applied to the grid, and the resulting grid at time $t_i$ may be displayed. The parameter value may also be interpolated separately for time $t_i$, substantially as described above with respect to the anchor grid. When reconstruction for all of the time points is concluded, the reconstructed grids may be displayed in sequence as a function of time, or in any other manner. Preferably, the reconstruction process continues while the anchor grid is displayed, so that a physician may use the reconstructed data without delay.

Preferably, as noted hereinabove, each data point includes at least is one physiological parameter, such as an indicator of the electrical activity in the heart, measured using functional portion 24 of catheter 20. After the map is constructed, as described above, the points on the grid, $G_1, G'_4, G'_7$, etc., that were associated with sampled points $S_1, S_2, S_6$, etc., are assigned the physiological parameter value of their respective sampled points. The non-associated grid points receive parameter values by interpolation between the values of the parameters of neighboring associated grid points in a manner similar to that described above. Alternatively or additionally, the non-associated grid points receive parameter values in a manner similar to the way they received their coordinates in flexible matching.

Further alternatively or additionally, the non-associated grid points are given parameter values using a zero-order-hold filling in method. Starting from the sampled points, all the surrounding grid points are given the same parameter value as the sampled point has, propagating outward until another grid point with a different parameter value is encountered. Thereafter, a Gaussian smoothing process is preferably applied to the parameter values. Thus, parameter values are given in a very simple method to all the grid points substantially without forfeiting visual clarity.

Thus, a 3D map is reconstructed showing both the geometrical shape of the heart chamber and local electrical parameters or other physiological parameters as a function of position in the heart. The local parameters may include electrogram amplitude, activation time, direction and/or amplitude of the electrical conduction vector, or other parameters, and may be displayed using pseudocolor or other means of graphic realization, as is known in the art. Preferably, a predefined color scale is associated with the parameter, setting a first color, e.g., blue, for high values of the parameter, and a second color, e.g., red, for low values of the parameter.

Figure 6:
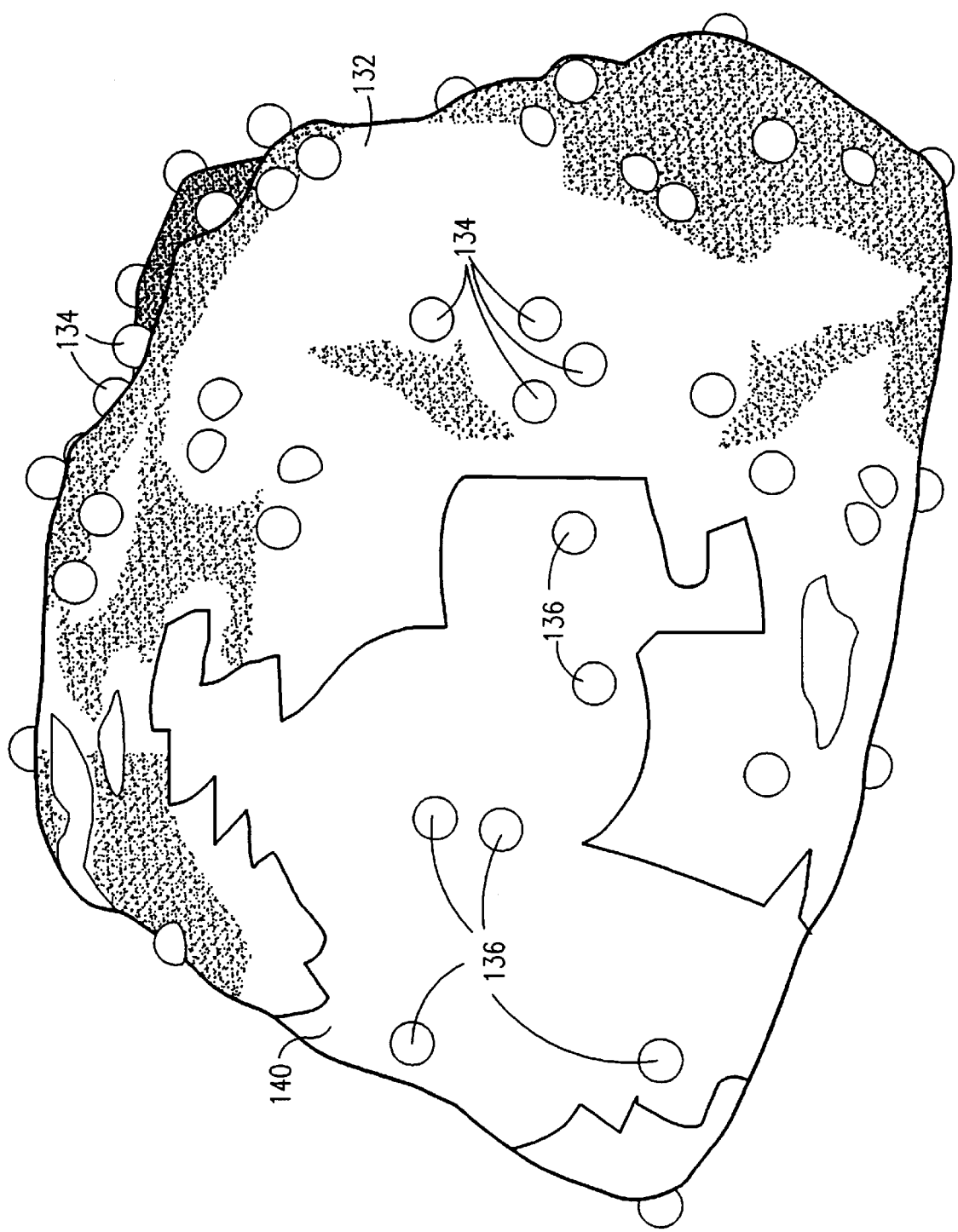
FIG. 6 is a schematic illustration of a displayed reconstructed heart volume, in accordance with a preferred embodiment of the present invention.

FIG. 6 is a schematic illustration of a displayed reconstructed heart volume 130, in accordance with a preferred embodiment of the present invention. A plurality of sampled points 134 are used to reconstruct a surface 132 of volume 130. A grid (not shown) is adjusted as described above to form surface 132. Preferably, each point on the grid receives a reliability value indicative of the accuracy of the determination. Further preferably, the reliability value is a function of the distance from the grid point to the closest sampled point on surface 132 and/or of a density of sampled points 134 in a vicinity of the grid point. Preferably, areas of surface 132 covered by less-reliable grid points, such as an area 140, are displayed as semi-transparent, preferably using □-blending. Due to the transparency, points 136 on an inner surface of volume 130 are displayed, being seen through volume 130. Preferably, the user may define the predetermined distance and/or sample density defining less-reliable points. Alternatively or additionally, different levels of semi-transparency are used together with a multi-level reliability scale.

Figure 7:
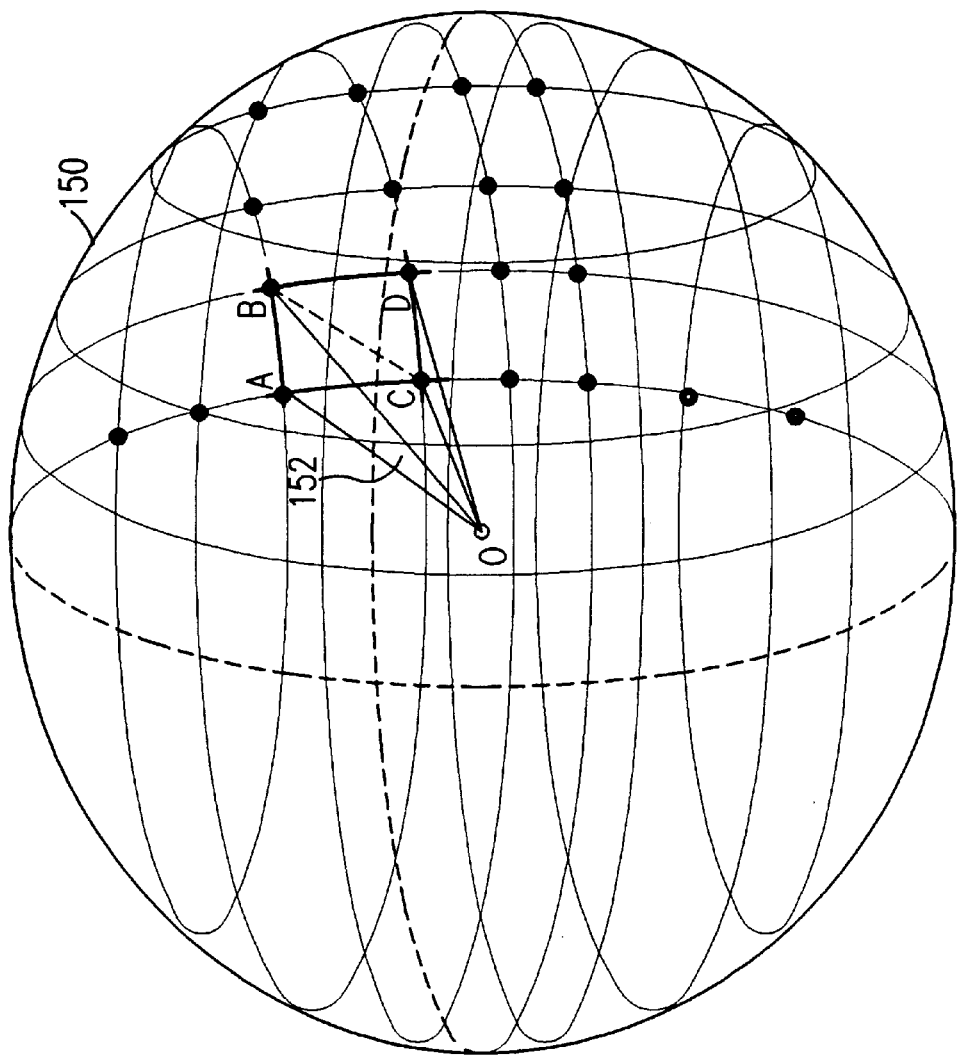
FIG. 7 is an illustration of a volume estimation method, in accordance with another preferred embodiment of the present invention.

FIG. 7 is a schematic illustration of a volume estimation method, in accordance with a preferred embodiment of the present invention. In some cases it is desired to estimate the volume encompassed by one or more reconstructed surfaces, for example, to compare the volume of a heart chamber at different time-points of the heart cycle. In FIG. 7 the reconstructed grid surface is represented, for clarity, by a ball 150. The surface of ball 150 is partitioned into quadrilaterals by the grid points, and these quadrilaterals are used for volume estimation. An arbitrary point O, in a vicinity of the surface, preferably within the volume, most preferably dose to the center of mass of ball 150, is chosen, thus defining a pyramid 152 for each quadrilateral on the surface of ball 150. An estimate of the sum of the volumes of pyramids 152 accurately represents the volume of ball 150.

Preferably, each quadrilateral is divided into two triangles, and the volume is estimated by summing the volumes of tetrahedrons defined by these triangles as bases and vertex O apex. Let $A_m$, $B_m$, $C_m$, denote the vertices of the m-th triangle arranged clockwise, so that the normals of the triangles point outward from the surface of ball 150. The volume V of ball 150 is estimated by equation (6):

$$V = \frac{1}{6} \sum_m (B_m - A_m) \times (C_m - A_m) \cdot (O - A_m) \quad (6)$$

Figure 8:
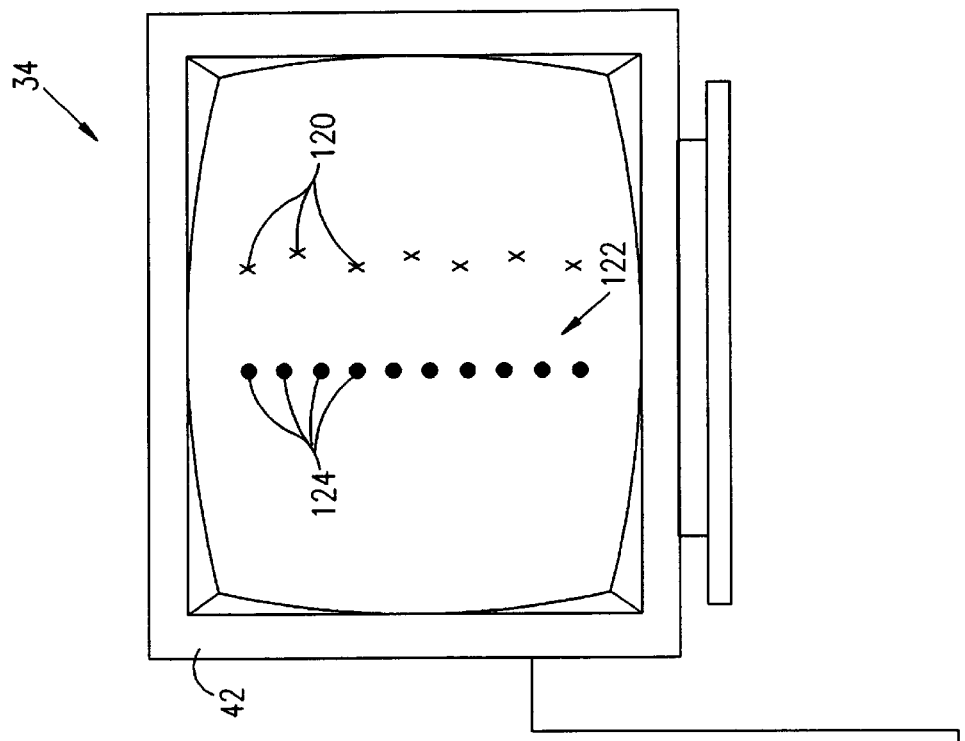
FIG. 8 is an illustration of a reconstruction procedure, in accordance with another preferred embodiment of the present invention.
Figure 8:
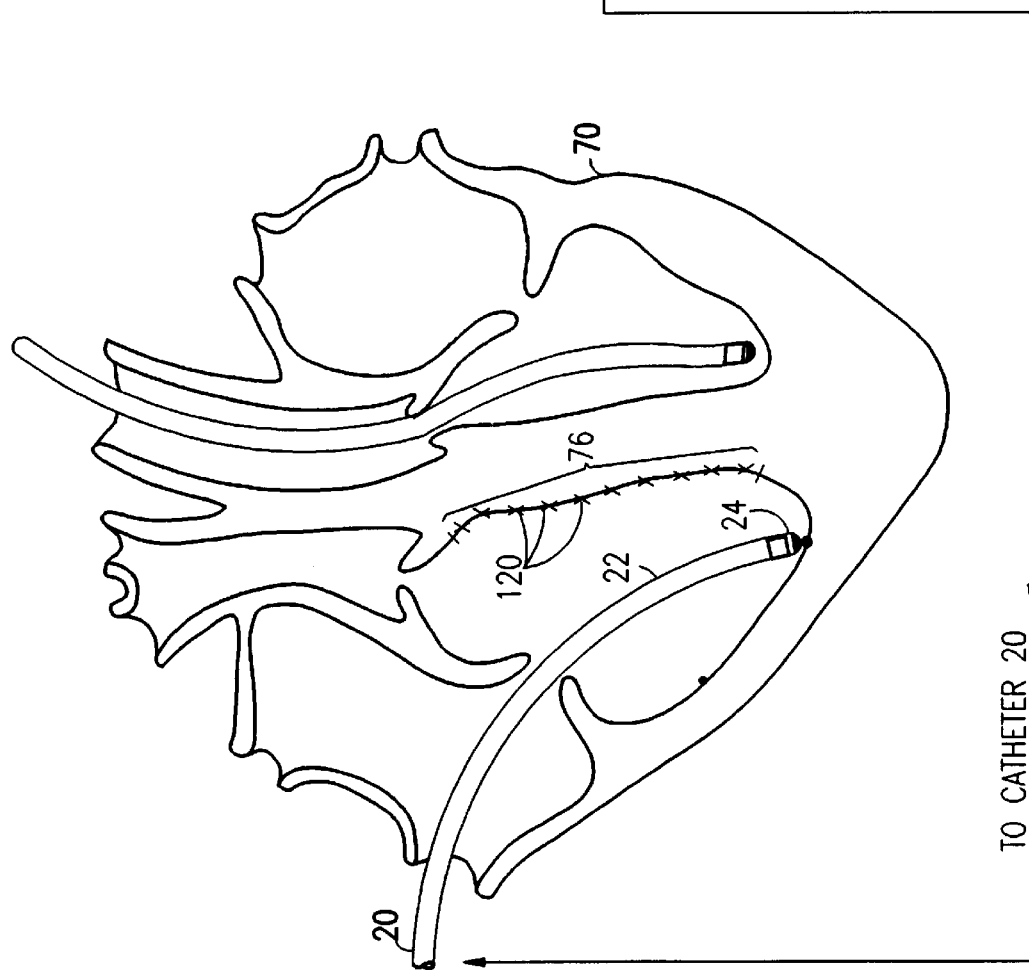

FIG. 8 is an illustration of a reconstruction procedure, in accordance with another preferred embodiment of the present invention. In this preferred embodiment the sampled points are known to be on a single, open surface, rather than surrounding a 3D volume, and therefore the beginning grid may comprise an open plane, rather than a closed curve. Catheter 20 is brought into contact with a plurality of locations on an inner wall 76 of heart 70, and the coordinates of these locations are determined to give sampled points 120. Preferably, a physician indicates to console 34 the direction from which catheter 20 contacts surface 76. Computer 36 accordingly generates an initial grid 122, which includes a plurality of grid points 124, such that all the grid points are preferably on one side of the sampled points. The adjustment procedure is performed substantially as described above, bringing grid points 124 to maximally resemble surface 76.

In a preferred embodiment of the present invention, the adjustment procedure may be performed step-by-step on display 42, allowing the physician to interrupt and direct the procedure if necessary.

It is noted that although the above description assumes that the data regarding the sampled points are acquired by the system which performs the reconstruction, the reconstruction procedure may also be performed on points received from any source, such as from a different computer, a library database or an imaging system. Furthermore, although preferred embodiments are described herein with reference to mapping of the heart, it will be appreciated that the principles and methods of the present invention may similarly be applied to 3D reconstruction of other physiological structure and cavities, as well as in non-medical areas of 3D image reconstruction.

It will thus be appreciated that the preferred embodiments of the invention described above are cited by way of example, and the full scope of the invention is limited only by the claims which follow.

What is claimed is:

1. A method of constructing a map of a body organ having a volume comprising:

using a position sensor to come into contact with a body organ, said sensor indicating its position in the body;

determining coordinates of a plurality of locations of the sensor on the organ, said coordinates having a configuration on a surface of the volume;

generating a grid of points defining a reconstruction surface in 3D space in proximity to the determined locations;

for each of the points on the grid, defining a respective vector, dependent on a displacement between one or more of the points on the grid and one or more of the locations; and adjusting the reconstruction surface by moving substantially each of the points on the grid responsive to the respective vector, so that the reconstruction surface is deformed to resemble the configuration of the surface.

2. A method according to claim 1, wherein generating the grid comprises acquiring an image of the volume and defining the reconstruction surface such that it resembles the image of the volume.

3. A method according to claim 1, wherein adjusting the surface comprises a rough adjustment stage and a flexible matching stage.

4. A method of constructing a map of a body organ having a volume comprising:

determining coordinates of a plurality of locations having a configuration on a surface of the volume;

generating a grid of points defining a reconstruction surface in 3D space in proximity to the determined locations;

for each of the points on the grid, defining a respective vector, dependent on a displacement between one or more of the points on the grid and one or more of the locations; and adjusting the reconstruction surface by moving substantially each of the points on the grid responsive to the respective vector, so that the reconstruction surface is deformed to resemble the configuration of the surface;

wherein adjusting the surface comprises a rough adjustment stage and a flexible matching stage; and wherein the rough adjustment stage comprises moving each point on the grid toward a respective weighted center of mass of the determined locations, wherein locations closer to the point on the grid are given larger weight.

5. A method according to claim 4, wherein moving each point comprises defining, for each of the points on the grid, a respective rough adjustment vector which comprises a weighted sum of vectors from the point to each of the determined locations and moving the points a distance proportional to the respective vector.

6. A method of constructing a map of a body organ having a volume comprising:

determining coordinates of a plurality of locations having a configuration on a surface of the volume;

generating a grid of points defining a reconstruction surface in 3D space in proximity to the determined locations;

for each of the points on the grid, defining a respective vector, dependent on a displacement between one or more of the points on the grid and one or more of the locations; and adjusting the reconstruction surface by moving substantially each of the points on the grid responsive to the respective vector, so that the reconstruction surface is deformed to resemble the configuration of the surface;

wherein adjusting the surface comprises a rough adjustment stage and a flexible matching stage; and wherein the flexible matching stage comprises selecting a grid point to e associated respectively with each of the determined locations.

7. A method according to claim 6, wherein the flexible matching stage comprises moving the selected grid points toward their respective determined locations.

8. A method according to claim 7, wherein the flexible matching stage comprises defining a displacement function which comprises a weighted sum of vectors, each vector connecting a location and its associated point.

9. A method according to claim 7, wherein the flexible matching stage comprises moving the grid points according to the displacement function so as to smooth the surface.

10. A method according to claim 1, wherein determining the coordinates comprises positioning a catheter tip at the plurality of locations.

11. A method according to claim 10, wherein positioning the catheter tip comprises positioning the catheter at a plurality of locations in a chamber of the heart.

12. A method according to claim 1, and comprising acquiring a signal indicative of a value of physiological activity at substantially each of the plurality of locations.

13. A method according to claim 1, wherein the volume is in motion, and wherein determining the coordinates comprises determining a correction factor responsive to the motion.

14. A method according to claim 13, wherein the motion comprises cyclic motion, and wherein determining the connection factor comprises determining a factor responsive to a cycle frequency of the motion.

15. A method according to claim 1, and comprising estimating a measure of the volume responsive to the reconstructed surface by choosing a point inside the grid and calculating the volumes of tetrahedrons defined by the chosen point and groups of three points on the grid which cover the entire grid surface.

16. Apparatus for constructing a map of a body organ having volume from coordinates of a plurality of determined locations having a configuration on a surface of the volume, comprising:

a position sensor for generating coordinates on the surface of the organ;

a processor, which receives the coordinates and generates a grid of points defining a reconstruction surface in 3D space in proximity to the determined locations, and which defines a respective vector for each of the points on the grid, dependent on a displacement between one or more of the points on the grid and one or more of the locations, and which adjusts the reconstruction surface by moving each of the points on the grid responsive to the respective vector, so that the reconstruction surface is deformed to resemble the configuration of the surface of the volume.

17. Apparatus as in claim 16, and comprising a display screen for displaying the adjusted surface.

18. Apparatus as in claim 16, and comprising an imaging device for acquiring an image of the volume, wherein the processor defines the grid initially such that it resembles the image of the volume.

19. Apparatus according to claim 16, and comprising a probe, which is brought into engagement with the surface to determine the locations thereon.

20. Apparatus according to claim 19, wherein the probe comprises said position sensor.

21. Apparatus according to claim 19, wherein the probe comprises a functional portion for acquiring a value of a physiological activity at the plurality of locations.

22. Apparatus according to claim 20, and comprising a reference catheter for registering the determined locations relative to a frame of reference associated with the volume.

* * * * *